(12) United States Patent
Yuan et al.

(10) Patent No.: US 11,207,562 B2
(45) Date of Patent: Dec. 28, 2021

(54) PELVIC FLOOR MUSCLE EXERCISE SYSTEM AND DETECTION DEVICE

(71) Applicant: VTrump Tech (Shanghai) Co., LTD., Shanghai (CN)

(72) Inventors: Jing Yuan, Shanghai (CN); Chao Li, Shanghai (CN); Zhu Zhang, Shanghai (CN); Junmin Zhang, Shanghai (CN); Yanwu Zhang, Shanghai (CN)

(73) Assignee: VTrump Tech (Shenghai) Co., LTD, Shanghai (CN)

( * ) Notice: Subject to any disclaimer, the term of this patent is extended or adjusted under 35 U.S.C. 154(b) by 920 days.

(21) Appl. No.: 15/745,433

(22) PCT Filed: Aug. 27, 2015

(86) PCT No.: PCT/CN2015/088239
§ 371 (c)(1),
(2) Date: May 23, 2018

(87) PCT Pub. No.: WO2017/008374
PCT Pub. Date: Jan. 19, 2017

(65) Prior Publication Data
US 2018/0264317 A1    Sep. 20, 2018

(30) Foreign Application Priority Data

Jul. 16, 2015   (CN) .......................... 201510418352.3
Jul. 16, 2015   (CN) .......................... 201520516667.7

(51) Int. Cl.
*A63B 23/20*      (2006.01)
*A61B 5/22*      (2006.01)
(Continued)

(52) U.S. Cl.
CPC ................ *A63B 23/20* (2013.01); *A61B 5/22* (2013.01); *A63B 71/0622* (2013.01);
(Continued)

(58) Field of Classification Search
CPC . A62B 23/20; A62B 2220/56; A62B 2220/51; A62B 2071/0655; A61B 5/227; A61B 5/1107
See application file for complete search history.

(56) References Cited

U.S. PATENT DOCUMENTS 4,356,826 A * 11/1982 Kubota .................... A61B 5/03
600/300
10,820,862 B2 * 11/2020 Rogers ................ A61B 5/1107
(Continued)

*Primary Examiner* — Sean P Dougherty
(74) *Attorney, Agent, or Firm* — Raymond Y. Chan; David and Raymond Patent Firm

(57) ABSTRACT

A physical training system for pelvic floor muscle, wherein the physical training system for pelvic floor muscle is capable of providing at least one optional exercising setting to user for making the physical training system for pelvic floor muscle can guide the user to accomplish at least one exercising movement, wherein the exercising setting is selected from a group of exercising settings, wherein the group of exercising settings comprises an exercising movement setting, an exercising time setting, an exercising intensity setting, an exercising frequency setting, an exercising guidance setting, an exercising auxiliary setting and an exercising feedback setting, wherein the physical training system for pelvic floor muscle comprises a processor and a Client, wherein the processor is capable of providing at least one optional exercising setting to user, wherein the exercising settings are set to be displayed on the Client.

18 Claims, 30 Drawing Sheets

(51) Int. Cl.
*A63B 71/06* (2006.01)
*A63B 24/00* (2006.01)
*A61H 19/00* (2006.01)
*A61B 5/11* (2006.01)

(52) U.S. Cl.
CPC ............ *A61B 5/1107* (2013.01); *A61B 5/227* (2013.01); *A61H 19/44* (2013.01); *A61H 2201/501* (2013.01); *A61H 2201/5046* (2013.01); *A61H 2201/5048* (2013.01); *A61H 2201/5061* (2013.01); *A61H 2201/5097* (2013.01); *A63B 24/0059* (2013.01); *A63B 24/0075* (2013.01); *A63B 2024/0068* (2013.01); *A63B 2071/063* (2013.01); *A63B 2071/0638* (2013.01); *A63B 2071/0655* (2013.01); *A63B 2220/51* (2013.01); *A63B 2220/56* (2013.01); *A63B 2225/20* (2013.01); *A63B 2225/50* (2013.01)

(56) References Cited

U.S. PATENT DOCUMENTS

| | | | | |
|---|---|---|---|---|
| 2003/0073881 A1* | 4/2003 | Levy | ............... | A61H 19/40 600/38 |
| 2004/0122341 A1* | 6/2004 | Walsh | ............... | A61B 5/227 600/591 |
| 2007/0185417 A1* | 8/2007 | Mittal | ............... | A61B 5/702 600/591 |
| 2008/0139876 A1* | 6/2008 | Kim | ............... | A61B 5/4337 600/29 |
| 2009/0281397 A1* | 11/2009 | Lavoisier | ............... | A61H 21/00 600/301 |
| 2011/0218395 A1* | 9/2011 | Stout | ............... | A61H 19/44 600/38 |
| 2014/0350333 A1* | 11/2014 | Stout | ............... | A61H 19/44 600/38 |
| 2015/0196802 A1* | 7/2015 | Siegel | ............... | A63B 21/0023 482/8 |
| 2015/0273270 A1* | 10/2015 | Brinkhaus | ............... | A63B 21/045 482/8 |
| 2015/0305971 A1* | 10/2015 | Davis | ............... | A61H 19/44 600/38 |
| 2016/0000642 A1* | 1/2016 | Zipper | ............... | A61H 23/0263 600/38 |
| 2016/0008664 A1* | 1/2016 | Siegel | ............... | A63B 24/0062 482/8 |
| 2016/0346610 A1* | 12/2016 | Iglesias | ............... | A61B 5/227 |

* cited by examiner

Sexy Superman

Primary Grade | Middle Grade | High Grade | Master Grade

Be applicable to women who seated in the office or female with low physical activity and fat female. The functions comprise avoiding vaginal and pelvic muscle subsidence, avoiding decrease in the amount of estrogen and ovarian dysfunction due to vaginal mucosal atrophy.

Start Training

PELVIC FLOOR MUSCLE EXERCISE SYSTEM AND DETECTION DEVICE

CROSS REFERENCE OF RELATED APPLICATION

This is a U.S. National Stage under 35 U.S.C. 371 of the International Application Number PCT/CN2015/088239, filed Aug. 27, 2015, which claims priority under 35 U.S.C. 119(a-d) to Chinese Application Number 201510418352.3, filed Jul. 16, 2015, and Chinese Application Number 201520516667.7, filed Jul. 16, 2015, the entire contents of each of which are expressly incorporated herein by reference.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to a medical equipment, and more particularly to a physical training system for pelvic floor muscle.

Description of Related Arts

In the medical field, the pelvic floor muscle includes a plurality of muscles, part of the pelvic muscle distributes in the urethra, vagina and anus to control the perfectly closing of the urethra and anus and the shrinking of the vagina. The pelvic floor muscle may be damaged due to infection, inflammation, trauma or excessive tearing, such as the excessive tearing caused by birth. The above human organs will not be able to act normal function once the pelvic muscle appearing problem, it could lead to bladder prolapse, rectocele, uterine prolapse, excrete difficult, cystitis, sexual response reducing and other chronic conditions such as discomfort.

As a result, it is necessary to possess an appropriate detecting device for pelvic floor muscle contraction in clinic. It can help doctors to assess the severity of the above disease and determine to use what kind of treatments to the patients.

But for most patients, their main problem is that the relaxation of the pelvic floor muscle is caused by common birth or age. For these patients, what they need is pelvic floor muscle training equipment to help them to recover the ability of tightening the contraction of the pelvic floor muscle but not drug.

An English patent which the application number is 1111532.6 states an electronic posture sensor or personal massager or pelvic floor trainer reactive to the squeezing or orientation or motion of the device, it can be worn or held adjacent to the body or even be inserted into the orifices of the pelvic region to detect and response to the wearer and the movement of the feedback equipment.

However, the electronic equipment which is disclosed by the above patent has many defects. First, the electronic equipment is mainly used to detect his/her movement or feedback to the equipment to improve the posture of the user (or exercisers). Therefore, the electronic equipment disclosed by the English patent which application number is 1111532.6 firstly needs to detect his/her movement or feedback to the equipment through sensor, and then remind him/her to adopt a better posture through its vibrating motor. In other words, the electronic equipment stated by the patent could not detect the contractility of the pelvic floor muscle directly and could not provide the detection result directly for the users (or exercisers), the equipment can only provide a reminder or a warning. Secondly, although the electronic equipment disclosed by the patent could be inserted into the female vagina also, it only plays a role in strengthening their pelvic floor muscles through providing directly positive feedback to them when the patients (or users) tighten the corresponding muscles successfully. In other words, the equipment disclosed by the English patent which application number is 1111532.6 only has a therapeutic effect through the vibration of the vibrating motor, it couldn't reply the detailed test results to the users (or exercisers) in order to make the users (or exercisers) exercising their pelvic floor muscles. Thirdly, the equipment disclosed by the English patent which application number is 1111532.6 needs to be preset or stored the correct posture in order to allow the equipment determining the users' (or exercisers') posture is correct or not. Finally, the equipment disclosed by the English patent which application number is 1111532.6 can only obtain a blurry and non-quantitative signal of the posture, and the posture signal can't be transmitted to an independent processor to be analyzed and visualized.

SUMMARY OF THE PRESENT INVENTION

A main advantage of the present invention is to provide a physical training system for pelvic floor muscle, wherein the physical training system for pelvic floor muscle is provided up for providing at least one optional exercising setting for the users to lead (or guide) the users to complete at least one exercising movements.

Another advantage of the present invention is to provide a physical training system for pelvic floor muscle, wherein the physical training system for pelvic floor muscle can provide a variety of optional exercise classes for the users.

Another advantage of the present invention is to provide a physical training system for pelvic floor muscle, wherein the physical training system for pelvic floor muscle can provide the optional exercise classes for different users.

Another advantage of the present invention is to provide a physical training system for pelvic floor muscle, wherein the users can choose or set up the optional exercising courses freely according to her/his own personal situation through the physical training system for pelvic floor muscle.

Another advantage of the present invention is to provide a physical training system for pelvic floor muscle, wherein the physical training system for pelvic floor muscle can provide the optional exercising courses for the users according to the user's personal situation.

Another advantage of the present invention is to provide a physical training system for pelvic floor muscle, wherein the physical training system for pelvic floor muscle can guide the users (or exercisers) to exercise according to the detection result by detecting the vaginal contractility of the users (or exercisers).

Another advantage of the present invention is to provide a physical training system for pelvic floor muscle, wherein the physical training system for pelvic floor muscle can provide at least one optional exercising settings or exercising guidelines according to the detection result by detecting the vaginal contractility of the users (or exercisers).

Another advantage of the present invention is to provide a physical training system for pelvic floor muscle, wherein the physical training system for pelvic floor muscle can provide at least one optional exercising settings or exercising guidelines for different users (or exercisers).

Another advantage of the present invention is to provide a physical training system for pelvic floor muscle, wherein the physical training system for pelvic floor muscle can provide at least one optional exercising settings or exercising guidelines for the users (or exercisers) according to the effect of the historical exercise.

Another advantage of the present invention is to provide a physical training system for pelvic floor muscle, wherein the physical training system for pelvic floor muscle can provide a visualization exercising effect for the users (or exercisers) to stimulate the users (or exercisers) to do exercising continually until complete its suggestion.

Another advantage of the present invention is to provide a physical training system for pelvic floor muscle, wherein the physical training system for pelvic floor muscle can provide a visualization video and/or audible audio for the users (or exercisers) to stimulate the users (or exercisers) to do exercising continually until complete its suggestion.

Another advantage of the present invention is to provide a physical training system for pelvic floor muscle, wherein the physical training system for pelvic floor muscle can provide an exercising reward conditionally to the users (or exercisers) to stimulate the users (or exercisers) to do exercising continually until complete its suggestion.

Another advantage of the present invention is to provide a physical training system for pelvic floor muscle, wherein the users (or exercisers) can send an instruction to the processor of the physical training system for pelvic floor muscle through a Client (Client-side) of the physical training system for pelvic floor muscle.

Another advantage of the present invention is to provide a physical training system for pelvic floor muscle, wherein the users (or exercisers) can set up the exercising model of the physical training system for pelvic floor muscle through the Client of the physical training system for pelvic floor muscle.

Another advantage of the present invention is to provide a physical training system for pelvic floor muscle, wherein the users (or exercisers) can set up the visualization type of the detection results of the vaginal contractility which is detected by the physical training system for pelvic floor muscle through the Client of the physical training system for pelvic floor muscle.

Another advantage of the present invention is to provide a device used to detect the vaginal contractility, wherein the device can accurately detect the vaginal contractility.

Another advantage of the present invention is to provide a device used to detect the vaginal contractility, wherein the device can be used to detect the vaginal contractility to help assessing the contractility of the pelvic floor muscle.

Another advantage of the present invention is to provide a device used to detect the vaginal contractility, wherein the device can be inserted into the vaginal to make the vagina give a contraction force to the pressure sensor of the device and make the contraction force can be detected.

Another advantage of the present invention is to provide a device used to detect the vaginal contractility, wherein the device is employed one or more thin film pressure sensors, so that the device can be miniaturized and wearable.

Another advantage of the present invention is to provide a device used to detect the vaginal contractility, wherein the device can change the analog signals from the pressure sensor into the digital signals, which make it easy to provide a visualization detection result for the users (or exercisers).

Another advantage of the present invention is to provide a device used to detect the vaginal contractility, wherein the device can simultaneously detect the contractility of the multiple sites of the vaginal inner wall to provide a comprehensive and objective status of the contractility of the pelvic floor muscle for the users or doctors. Therefore, the device can also help her (or him) to assess her (or his) disease condition even if the users are ordinary women (or men).

Additional advantages and features of the invention will become apparent from the description which follows, and may be realized by means of the instrumentalities and combinations particular point out in the appended claims.

According to the present invention, the foregoing and other objects and advantages are attained by providing a physical training system for pelvic floor muscle, wherein the physical training system for pelvic floor muscle comprises:

a detector; and a processor, wherein the detector is provided to detect contractility of vaginal inner wall of the user and generate a real-time detecting data, and send the real-time detecting data to the processor, the processor is capable of receiving the real-time detecting data and process visually the real-time detecting data, wherein the real-time detecting data which is visually processed by the processor can be displayed by one Client for making the real-time detecting data be sensed by user.

The present invention further provides a device used to detect vaginal contractility of female, comprising:

a receiving body;

a pressure detector; and a data processing unit, wherein the receiving body defines a receiving chamber, the pressure detector is provided within the receiving chamber, wherein the pressure detector is provided to detect pressure which is applied on the pressure detector by vaginal inner wall and generate a real-time detecting signal, the data processing unit is capable of receiving the real-time detecting signal from the pressure detector and transmit the real-time detecting signal to a receiver.

The present invention further provides a method of detecting vaginal contractility, which comprises following steps:

(a) inserting a detector into user's vagina;

(b) detecting vaginal contractility through a thin film pressure sensor of a pressure detector of said detector and obtaining a detecting signal through the pressure detector, wherein the contractility is applied on the detector by inner wall of user's vagina; and (c) transmitting the real-time detecting signal to a processor, wherein the processor is provided to process the real-time detecting signal for making the real-time detecting signal to be visual and to be displayed, which makes the real-time detecting signal can be sensed by the user.

Based on this, in view of the above technical problems, the present invention further provides a detecting device of female's pelvic floor muscle.

The present invention adopts the following technical scheme for solving the above technical problems:

A detecting device of female's pelvic floor muscle, comprising:

a plurality of thin film pressure sensors, the multiple film pressure sensors are respectively arranged on the surfaces around the detecting carrier, and the surface of the thin film pressure sensor is covered with medical silica gel layer, every thin film pressure sensor connects to the analog-digital converting module through a voltage amplifying circuit;

analog-digital converting module, the analog-digital converting module connects to the voltage amplifying circuit for converting measuring voltage which is output through the voltage amplifying circuit to digital signal of the measuring voltage;

master controlling module, the master controlling module connects to the analog-digital converting module for obtaining the digital signal of the measuring voltage from the analog-digital converting module, the master controlling module can calculate the pressure values imposed to the thin film pressure sensor through the formulas, and control the data transmitting module send the voltage values to a data processing terminal:

$$Fs^{-b} = -(V_T * R_F)/(a * Vout);$$

$$F = Fs - Fc; (F \text{ is final pressure})$$

Wherein the Vout is measuring voltage, $V_T$ is the voltage loaded into the thin film pressure sensor, $R_F$ is the resistance of the signal amplifying module, a and b are the characteristic constants of the thin film pressure sensor, the value range of a is [1,100000], the value range of b is [0.1,100].

$$Vout = -V_T * (R_F/R_S) \quad (1)$$

Wherein the Vout is the measuring voltage, the $V_T$ is the reference voltage loaded into the thin film pressure sensor, the $R_F$ is the reference resistance of the amplifying circuit, the $R_S$ is the resistance of the thin film pressure sensor.

The data transmitting module is connected with the master controlling module for sending the pressure values from the master controlling module to a data processing terminal.

The scheme also comprises a data processing terminal, the data processing terminal wired or wireless connects to the data transmitting module.

The data processing terminal is computer, smartphone or tablet computer, Virtual Reality device, Augmented Reality device, Mixed Reality device, etc.

The scheme also comprises a data storage module which is connected with the master controlling module for storing the pressure values.

The master controlling module and the data transmitting module can be integrated into a single chip or different chips.

The multiple thin film pressure sensors connected with each other in series.

The multiple thin film pressure sensors connected with each other in parallel.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1:
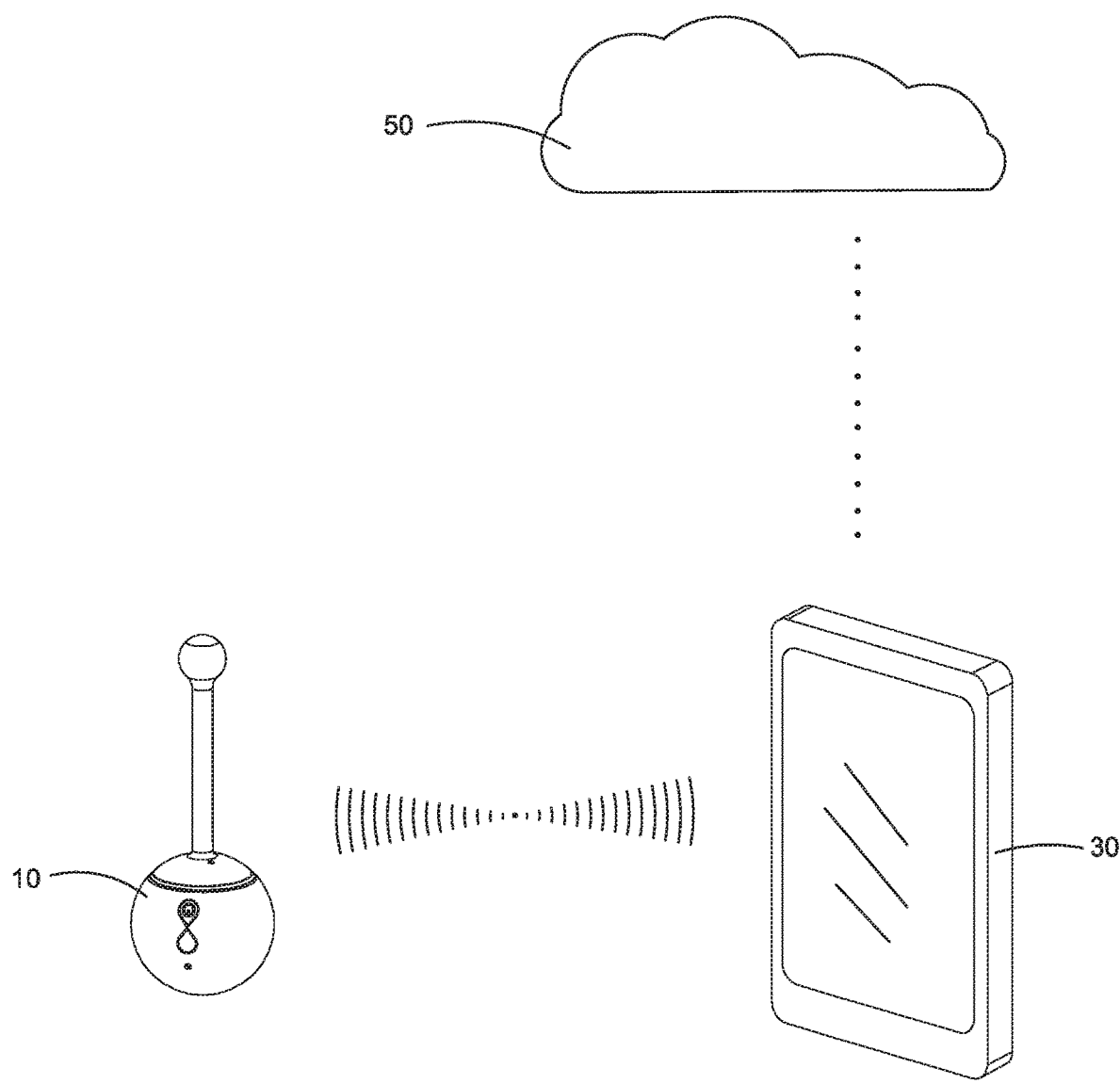
FIG. 1 is a perspective view of a physical training system for pelvic floor muscle according to a preferred embodiment of the present invention.
Figure 2:
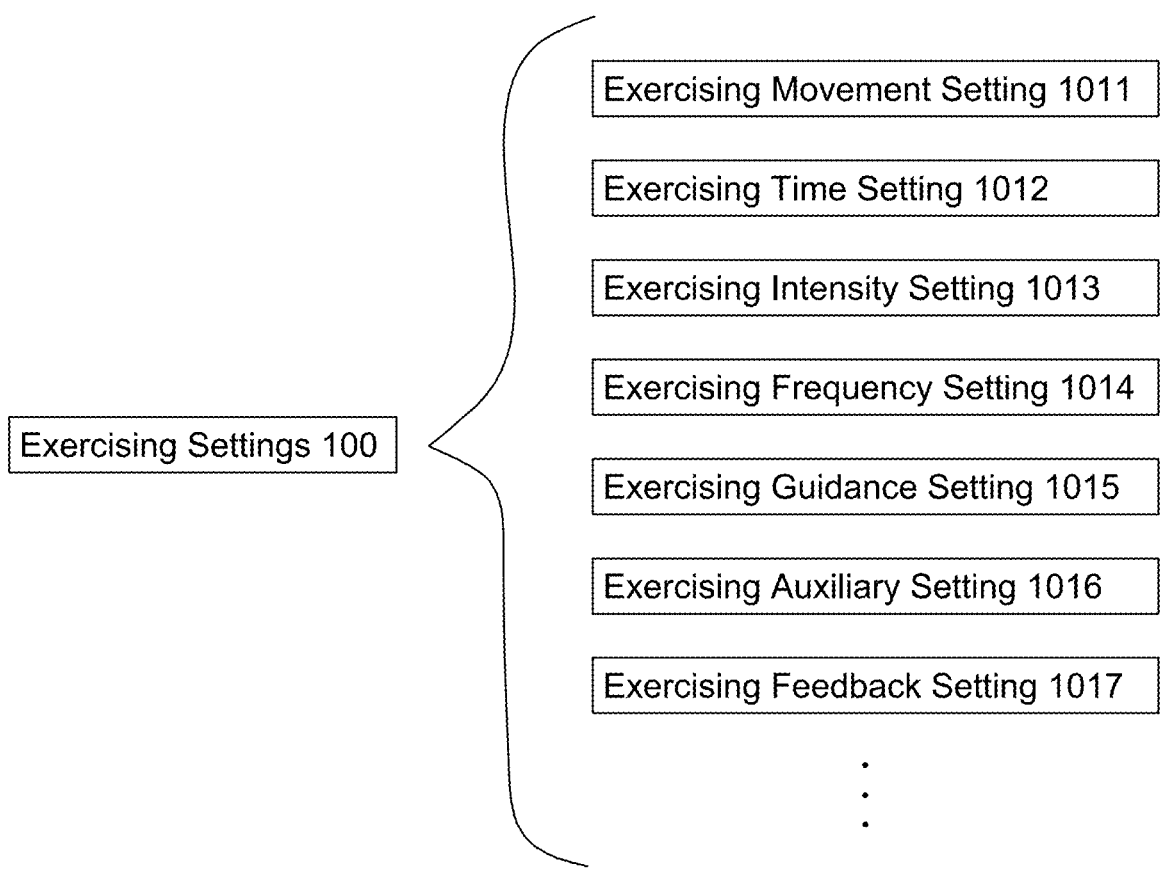
FIG. 2 is a diagram of an optional exercising setting provided by the physical training system for pelvic floor muscle according to the above preferred embodiment of the present invention.

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

The "exercising movement" described in the present invention refers to the physical activity completed by the user in order to achieve the exercising purpose or implement the exercising effect, such as the cycle of the vaginal contraction and relaxation. The "effective exercising movement" described in the present invention refers to the exercising movement detected by the physical training system of the present invention. The "standard exercising movement" described in the present invention refers to the effective exercising movement which is accord with one standard.

Referring to FIG. 1 to FIG. 12 of the drawings, a physical training system for pelvic floor muscle according to a preferred embodiment of the present invention is illustrated, in which the physical training system for pelvic floor muscle is provided to be used for providing at least one optional exercising setting 101 to the users in order to make the physical training system for pelvic floor muscle lead (or guide) the user to complete at least one exercising movement, wherein the exercising setting 101 is selected from a group of exercising settings 100, wherein the group of exercising settings 100 comprises but it is not limited to an exercising movement setting 1011, an exercising time setting 1012, an exercising intensity setting 1013, an exercising frequency setting 1014, an exercising guidance setting 1015, an exercising auxiliary setting 1016 and an exercising feedback setting 1017 or the combination of them. In other words, the physical training system for pelvic floor muscle can provide at least one exercising setting 101 selected by the user to the user in order to make the physical training system for pelvic floor muscle lead (or guide) the user to complete at least one exercising movement. As mentioned above, in the present invention, the exercising movement refers to the physical activity completed by the user in order to achieve the exercising purpose or implement the exercising effect, such as the cycle of the vaginal contraction and relaxation. In some cases, the exercising movement may be the other physical activities of the exercise of the pelvic floor muscle. Therefore, the physical activity of the present invention can be the muscle exercising activity accomplished by the user when the user completes the Kegel Exercise movement. The exercising movement setting 1011 is preferably related to comprise but not limit to the vaginal contraction and relaxation movement in one exercising period and/or the cycle number of the vaginal contraction and relaxation movement needed to be done in one group exercising movement. For example, in one exercising period, it is need to accomplish two hundred cycles of the vaginal contraction and relaxation movements, the two hundred cycles of the vaginal contraction and relaxation movements are further divided into five groups to be accomplished, so it is need to accomplish forty cycles of vaginal contraction and relaxation movements in one group exercising movement. The exercising time setting 1012 is preferably related to comprise but not limit to the exercising duration of every exercise, such as one exercising duration time is 20 minutes, the user should conduct cycle of the vaginal contraction and relaxation movements continually in the 20 minutes, in order to insure the training for pelvic floor muscle can conduct continually and the training for pelvic floor muscle is effective or helpful. The exercising intensity setting 1013 is preferably related to comprise but not limit to one single exercising movement, for example the duration of one single vaginal contraction, the intensity of one single exercising movement, such as one single vaginal contraction force and/or the number of the effective exercising movement (or the number of the standard exercising movement). The exercising frequency setting 1014 is preferably related to comprise but not limit to the training number for pelvic floor muscle through using the physical training system for pelvic floor muscle in unit time, for example one day, one week or one month. Therefore, the preferred unit described in the present invention is one day, one week or one month and so on. The exercising guidance setting 1015 is preferably related to comprise but not limit to the guided way produced by the physical training system for pelvic floor muscle guides the user to train the pelvic floor muscle, such as the physical training system for pelvic floor muscle can provide a guideline in the form of voice to the user. In some embodiments, the voice guide is with a background voice such as smoothing music when the physical training system for pelvic floor muscle uses the voice to guide, in order to provide an exercising guiding environment to the user which is consistent with the user's interest. The exercising auxiliary setting 1016 is preferably related to the auxiliary means which is provided by the physical training system for pelvic floor muscle to the user, wherein the auxiliary means which is provided by the physical training system for pelvic floor muscle to the user can help the user to accomplish the exercising movement, such as the physical training system for pelvic floor muscle can provide the stimulation of image, voice or touch to the user when the user is exercising his/her pelvic floor muscle, in order to make the user more excited and help the user to accomplish the exercising movement. The exercising feedback setting 1017 is preferably related to the exercising effect (or result) which is reported to the user by the physical training system for pelvic floor muscle, such as the physical training system for pelvic floor muscle can give a voice feedback when the user accomplished one effective exercising movement, and it can give another voice feedback when the user accomplished one standard exercising movement, in order to remind or guide the user to accomplish the exercising movement better. Preferably, the physical training system for pelvic floor muscle will give a positive exercising feedback when the user accomplishes the exercising movement in a preset unit time, wherein the positive exercising feedback is voice, image or word and so on. More preferably, the physical training system for pelvic floor muscle will give a negative exercising feedback when the user doesn't accomplish the exercising movement or accomplish the exercising movement unsuccessfully in a preset unit time, wherein the negative exercising feedback is voice, image or word and so on.

Figure 3:
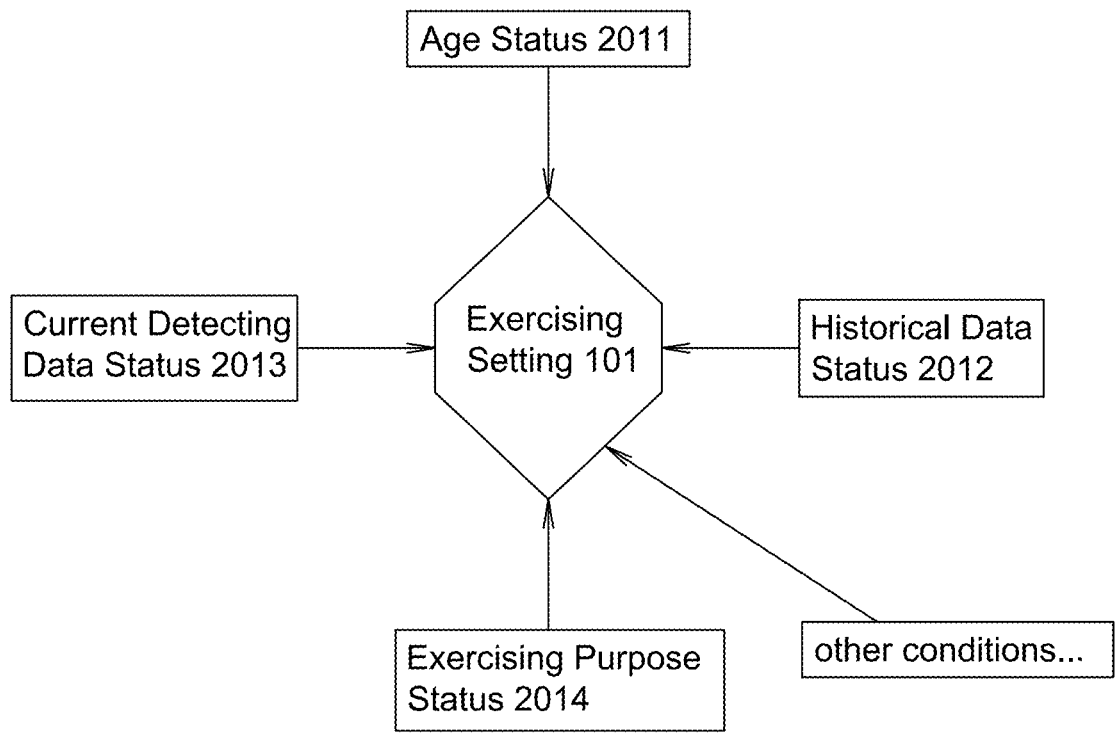
FIG. 3 is a generative diagram of the optional exercising setting provided by the physical training system for pelvic floor muscle according to the above preferred embodiment of the present invention.
Figure 4:
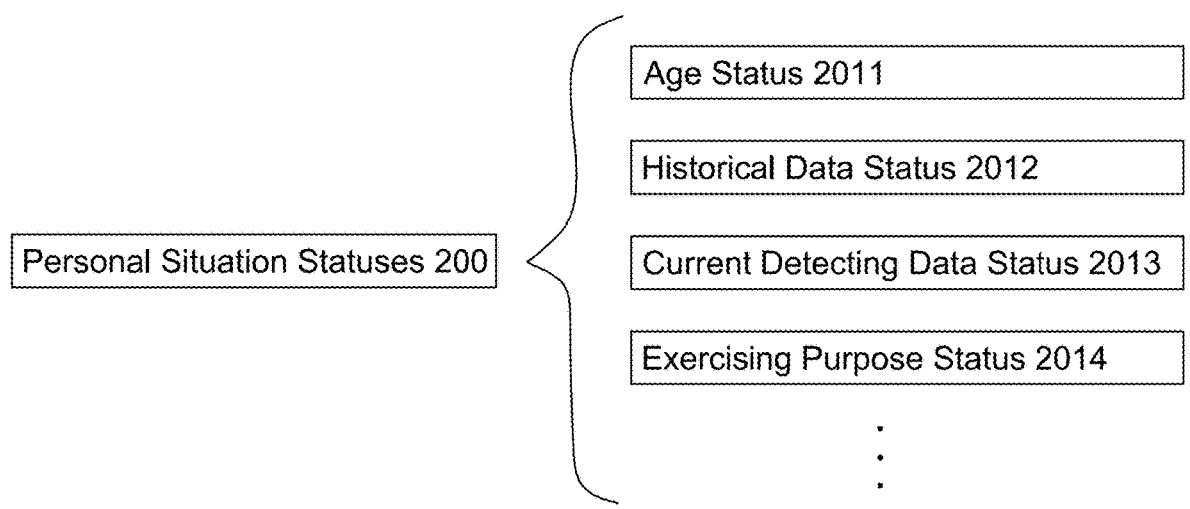
FIG. 4 is a diagram of the personal conditions provided by the physical training system for pelvic floor muscle according to the above preferred embodiment of the present invention.
Figure 5:
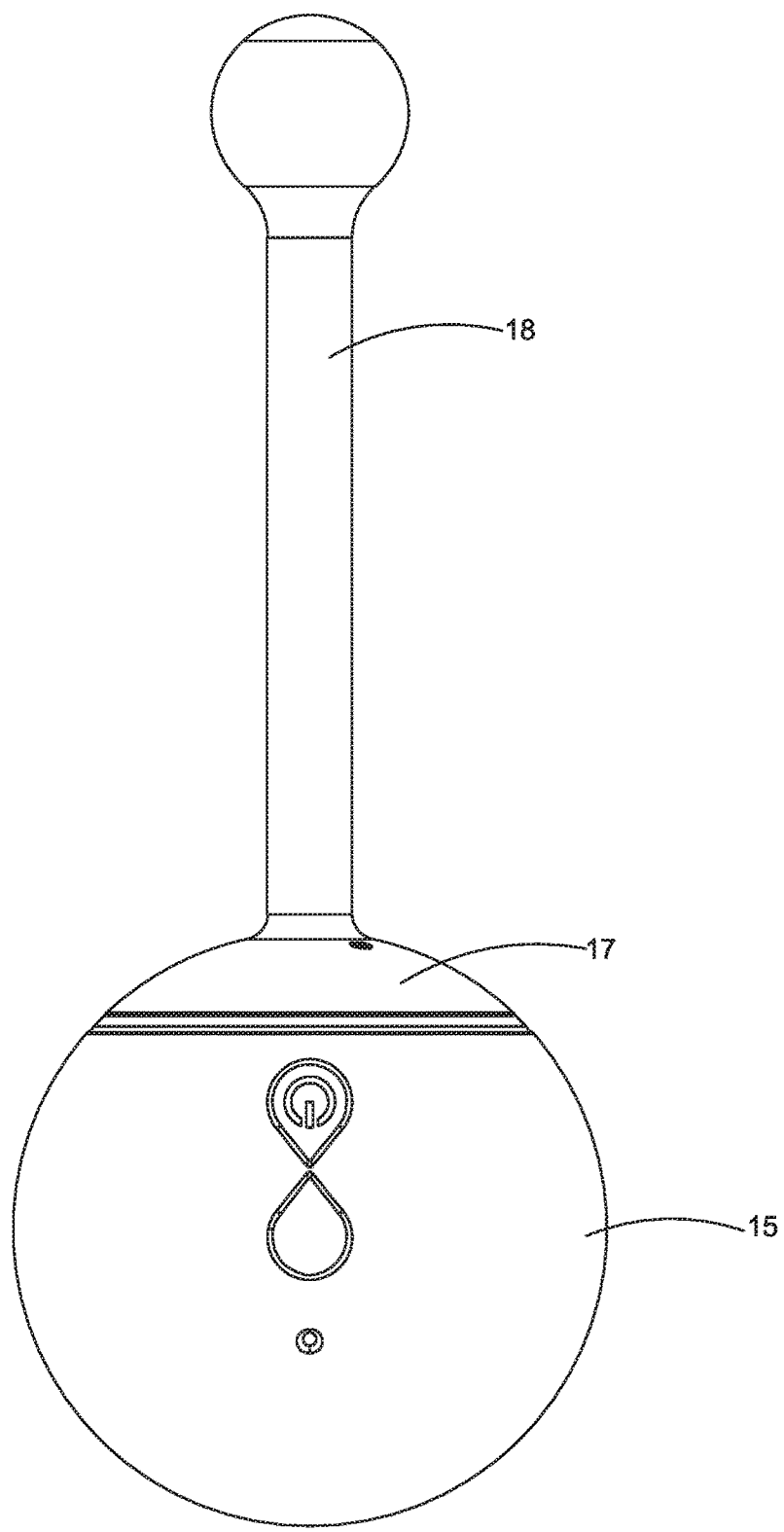
FIG. 5 is a front view of a detector of the physical training system for pelvic floor muscle according to the above preferred embodiment of the present invention.

Referring to FIG. 3 and FIG. 4 of the drawings, the physical training system for pelvic floor muscle is provided to provide an optional exercising setting 101 according to the user's personal situation 201, wherein the personal situation 201 is selected from a combination of personal situations 200, wherein the combination of personal situations 200 comprises but not limit to an age status 2011, a historical data status 2012, a current detecting data status 2013 and an exercising purpose status 2014. The age status 2011 generally refers to the user's age. The historical data status 2012 generally refers to the exercising settings or the group of exercising settings which are chosen by the user with a certain of time in the past, but it also refers to the user's exercising schedule with a certain of time in the past.

The current detecting data status 2013 generally refers to the user's physical condition reflected by the real-time detecting data which is obtained from the current physical training system detects the user's health, such as the biggest contractility (or pressure) inside the user's vagina reflects the degree of relaxation of the user's pelvic floor muscle. The exercising purpose status 2014 generally refers to the exercising purpose which is achieved through the user uses the physical training system for pelvic floor muscle to exercise, such as to recover the vaginal tearing and relaxation which is caused by parturition. The physical training system for pelvic floor muscle is provided to provide the optional exercising setting 101 or the combination of the optional exercising settings 101 according to the user's personal situation 201. In other words, the physical training system for pelvic floor muscle can automatically provide the optional exercising setting 101 according to the user's personal situation 201, such as the age and so on, in order to guide the user to use the physical training system for pelvic floor muscle to exercise his/her pelvic floor muscle. Preferably, the physical training system for pelvic floor muscle will automatically provide one acquiescently exercising setting 101 (or combination) in the case of the physical training system for pelvic floor muscle is failed to get the user's personal situation 201. In some embodiments, the user can initiatively set the exercising setting 101 (or combination) of the physical training system for pelvic floor muscle through the user chooses to input order to the physical training system for pelvic floor muscle, such as the user can use the keyboard, mouse, touch screen and other input equipments to input the order into the data processor of the physical training system for pelvic floor muscle, such as processor, and set the exercising setting 101 (or combination) of the physical training system for pelvic floor muscle. Optionally, the user can input order to the physical training system for pelvic floor muscle and set the exercising setting 101 (or combination) of the physical training system for pelvic floor muscle via using a touch screen 31. Optionally, the user can also input order to the physical training system for pelvic floor muscle and set the exercising setting 101 (or combination) of the physical training system for pelvic floor muscle via inputting the sound wave or electromagnetic wave which is carried or coded the order to the physical training system for pelvic floor muscle.

Referring to FIG. 5 to FIG. 12 of the drawings, the physical training system for pelvic floor muscle according to the preferred embodiment of the present invention comprises a detector 10 and a processor 20, wherein the detector 10 is provided to detect the contractility of vaginal inner wall of the user and generate a real-time detecting data, and the detector 10 sends the real-time detecting data to the processor 20, the processor 20 is provided to receive the real-time detecting data and process the real-time detecting data into visualization, wherein the real-time detecting data which is visually processed by the processor 20 can be displayed by a Client 30 to make the real-time detecting data to be able to be sensed by the user. The processor 20 of the physical training system for pelvic floor muscle is further set to process the received real-time detecting data and obtain the current detecting data status 2013, and provide at least one optional exercising setting 1001 according to the current detecting data status 2013. Understandably, the current detecting data status 2013 can be restored in the storage component of the physical training system for pelvic floor muscle, such as a memorizer, in order to be used as the historical data status 2012 in the future. Preferably, the current detecting data status 2013 stored in the memorizer can be read by the processor 20 of the physical training system for pelvic floor muscle. In other words, the detector 10 and the processor 20 are connected with each other and can communicate with each other, which makes the real-time detecting data can be transmitted to the processor 20 when the detector 10 detects the contractility of vaginal inner wall of the user can generates the real-time detecting data. Understandably, the connection and the communication between the detector 10 and the processor 20 can be the connection with cable or electricity, or the connection may be realized through an electronic network.

Understandably, the processor 20 is computerized or programmed to be set to provide at least one optional exercising setting 101 (or combination) to the user according to the current detecting data status 2013, in order to guide the user to accomplish at least one exercising movement. Preferably, the processor 20 is further capable of providing a visual exercising effect to the user to stimulate the user to do exercising continually to complete its suggested exercising, such as the exercising movement. More preferably, the visual exercising effect is the stimulation of the visual video and/or audible audio. In some embodiments, the physical training system for pelvic floor muscle can provide an exercising reward conditionally to the users (or exercisers) to stimulate the users (or exercisers) to do exercising continually to complete its suggested exercising, wherein the reward is voice, image, word (or figure) and/or voice. In other embodiments, the user can also use one Client 30 to send out an order to the processor 20 to set the physical training system for pelvic floor muscle, such as setting the exercising model of the physical training system for pelvic floor muscle or the visual type of the detecting result of the vaginal contractility which is detected by the physical training system for pelvic floor muscle.

Referring to FIG. 5 to FIG. 12 of the drawings, the detector 10 of the physical training system for pelvic floor muscle according to the preferred embodiment of the present invention comprises an receiving body 11, a pressure detector 12 and a data processing unit 13, wherein the receiving body 11 defines a receiving chamber 110, the pressure detector 12 is provided within the receiving body 11, the data processing unit 13 is provided within the receiving chamber 110, wherein the pressure detector 12 is provided to detect the pressure which is applied on vaginal inner wall by the vaginal inner wall and generates a real-time detecting signal, the data processing unit 13 is capable of receiving the real-time detecting signal from the pressure detector 12 and transmit the real-time detecting signal to a receiver, such as the above processor 20. The data processing unit 13 is generally capable of transmitting figure signal. As known as the person skilled in the art, the data processing unit 13 is also set to transmit the analog electronic signal. Therefore, the real-time detecting signal can be transmitted by the data processing unit 13, and the real-time detecting signal can be analog electronic signal or figure signal.

Referring to FIG. 5 to FIG. 12 of the drawings, the data processing unit 13 of the detector of the physical training system for pelvic floor muscle according to the above preferred embodiment of the present invention comprises a first communicating module 131, wherein the first communicating module 131 of the data processing unit 13 is capable of receiving the real-time detecting signal from the pressure detector 12 and transmit the real-time detecting signal to the processor 20. The first communicating module 131 is generally set to transmit the figure signal. As known as the person skilled in the art, the first communicating module 131 is also set to transmit the analog electronic signal. Therefore, the real-time detecting signal can be transmitted by the first communicating module 131, and the real-time detecting signal can be analog electronic signal or figure signal.

Figure 6:
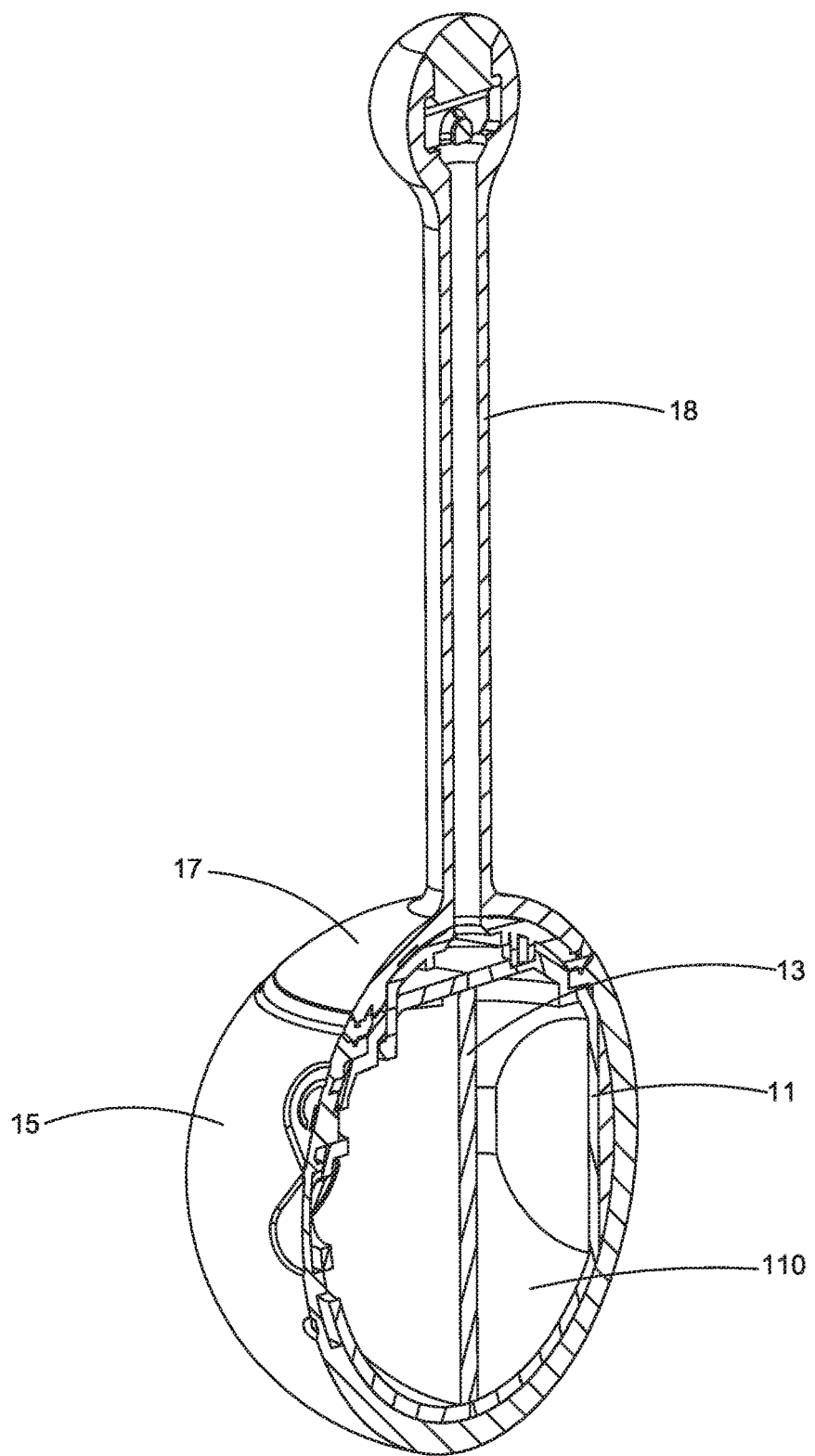
FIG. 6 is a sectional view of the detector of the physical training system for pelvic floor muscle according to the above preferred embodiment of the present invention.
Figure 7:
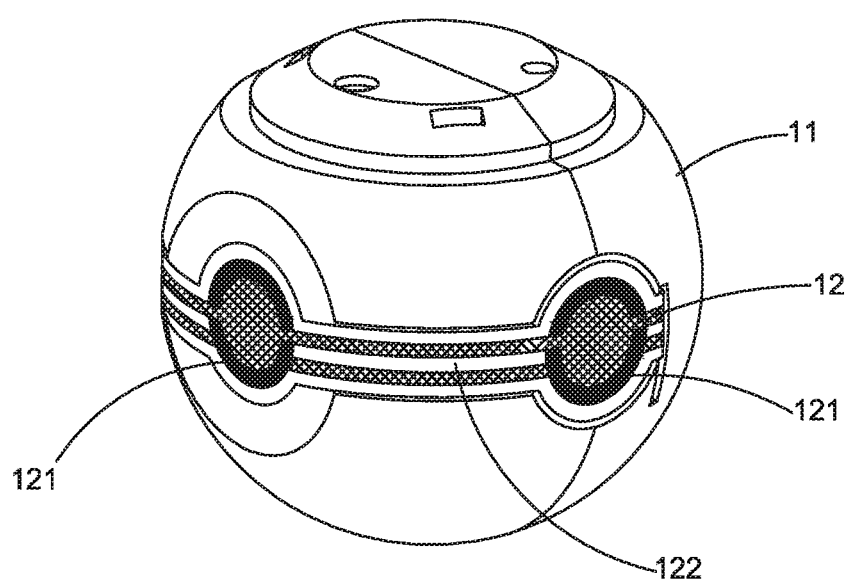
FIG. 7 is a perspective view of a receiving body of the detector of the physical training system for pelvic floor muscle according to the above preferred embodiment of the present invention, wherein the drawing shows the pressure sensor of the detector is provided within the receiving body of the detector.
Figure 8:
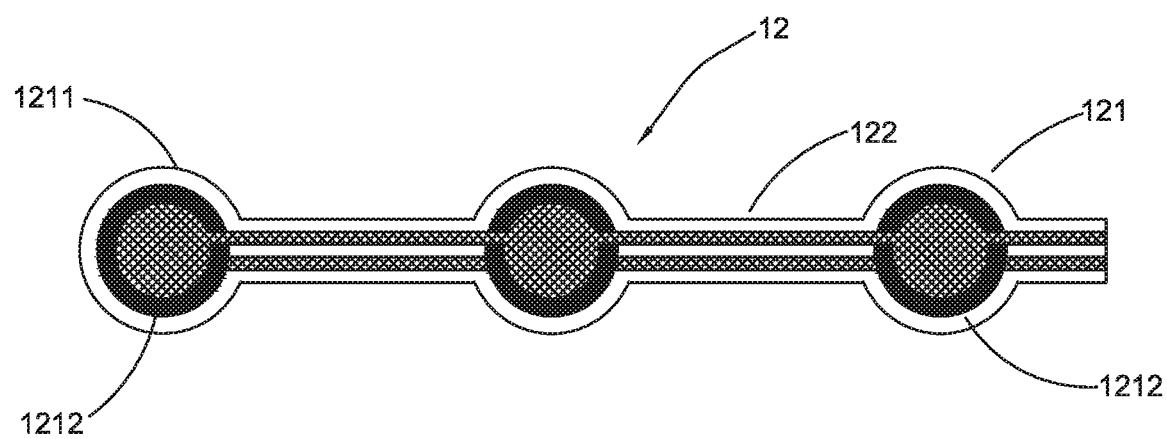
FIG. 8 is a front view of the pressure sensor of the detector of the physical training system for pelvic floor muscle according to a preferred embodiment of the present invention.
Figure 9:
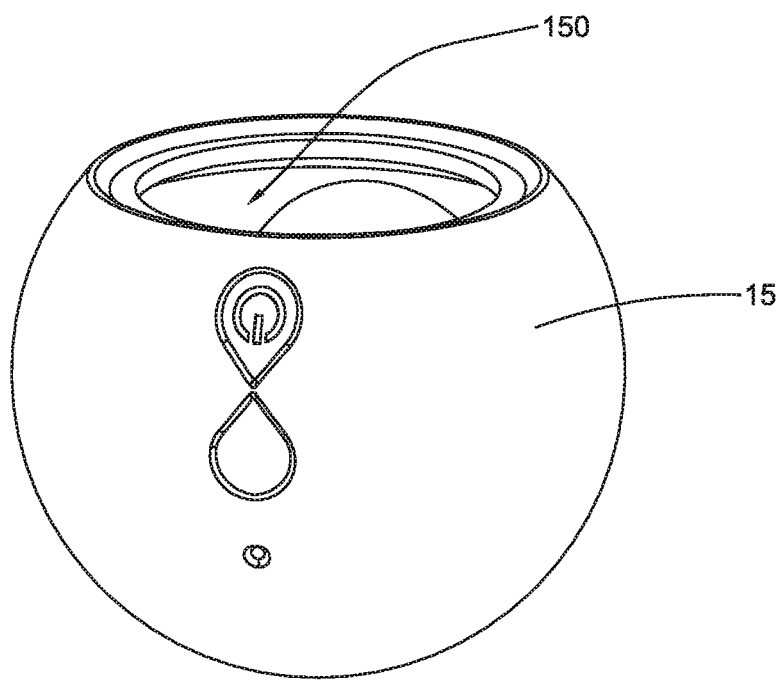
FIG. 9 is a front view of a coat of the detector of the physical training system for pelvic floor muscle according to the above preferred embodiment of the present invention.
Figure 10:
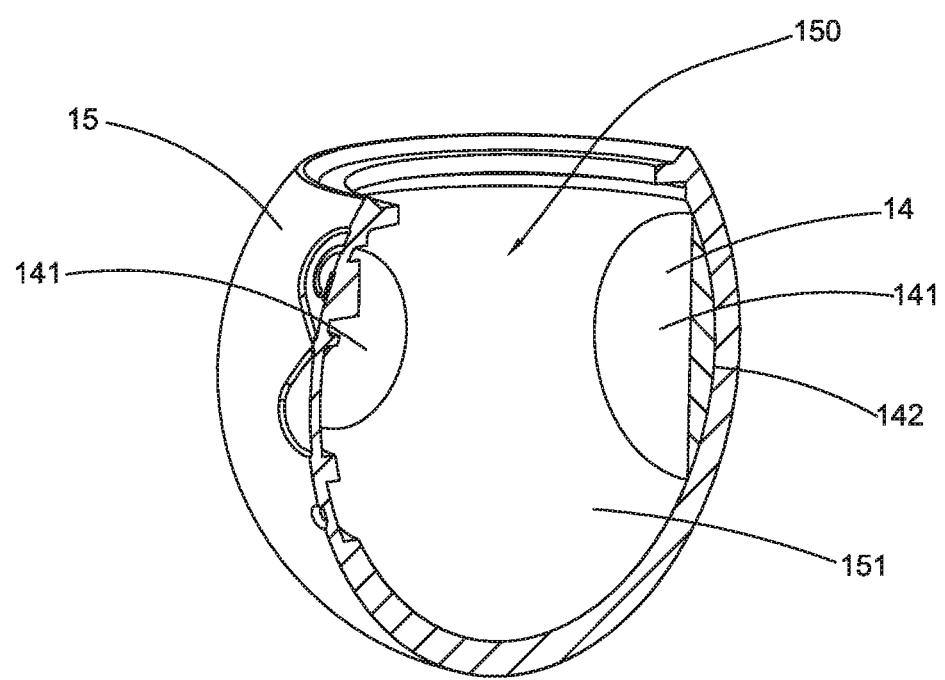
FIG. 10 is a sectional view of the pressure sensor of the detector of the physical training system for pelvic floor muscle according to the above preferred embodiment of the present invention.
Figure 11:
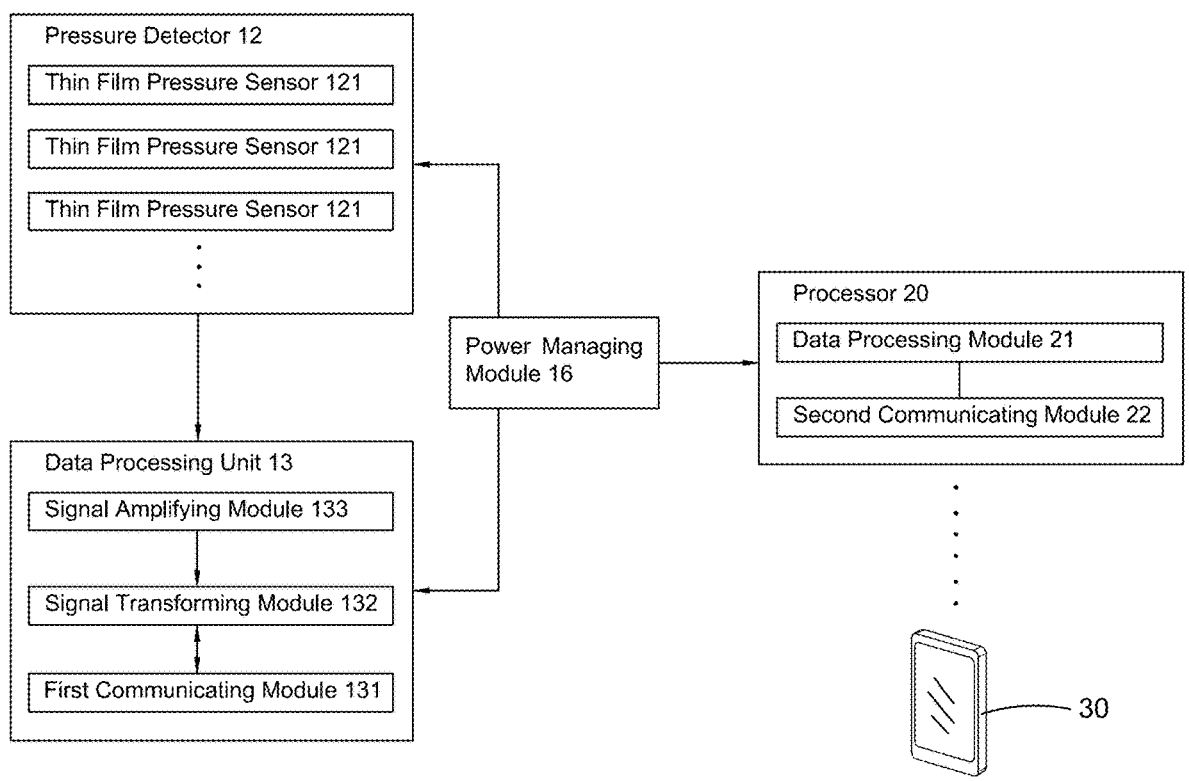
FIG. 11 is a schematic diagram of circuit connection between various components of the detector of the physical training system for pelvic floor muscle according to the above preferred embodiment of the present invention.
Figure 12:
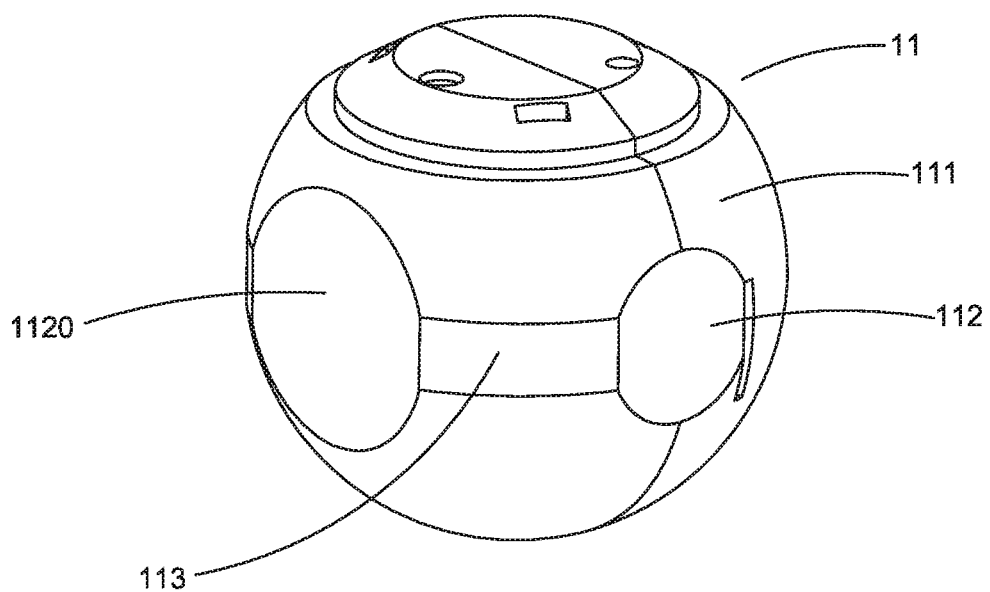
FIG. 12 is a perspective view of the receiving body of the detector of the physical training system for pelvic floor muscle according to the above preferred embodiment of the present invention.

Referring to FIG. 6 to FIG. 8 of the drawings, the pressure detector 12 of the detector comprises a plurality of thin film pressure sensors 121, wherein every thin film pressure sensor 121 of the pressure detector 12 is connected electrically with the data processing unit 13. Preferably, every thin film pressure sensor 121 of the pressure detector 12 which is also connected with each other in series is connected electrically with the data processing unit 13. As known as the person skilled in the art, the data processing unit 13 can receive the contractility detecting signal of the vaginal inner wall from the thin film pressure sensor 121 of the pressure detector 12. Furthermore, the thin film pressure sensors 121 of the pressure detector 12 are all connected electrically with the first communicating module 131 of the data processing unit 13. Therefore, the thin film pressure sensor 121 of the pressure detector 12 which are connected in parallel are connected electrically with the first communicating module 131 of the data processing unit 13.

Referring to FIG. 6 to FIG. 12 of the drawings, the receiving body 11 of the detector 10 has an outer wall 111 and comprises a plurality of installing positions 112 defined on the outer wall 111 of the receiving body 11, wherein every outer wall 111 has an installing surface 1120, wherein the thin film pressure sensors 121 of the pressure detector 12 are arranged on the installing surface 1120 respectively.

It is worth noting that the thin film pressure sensor 121 preferably has an installing side 1211 and an inductive side 1212, wherein the installing side 1211 is provided on the installing position 112 of the receiving body 11, wherein the contractility from the vagina can be directly or indirectly applied on the inductive side 1212 of every thin film pressure sensor 121.

Referring to FIG. 6 to FIG. 12 of the drawings, the detector 10 further comprises a plurality of force transmitting elements 14, wherein the force transmitting elements 14 are respectively provided on the thin film pressure sensors 121 of the pressure detector 12, wherein the every force transmitting element 14 has an operating side 141 and an outer side 142, wherein the operating side 141 of the force transmitting element 14 is pressed down the thin film pressure sensors 121, wherein the outer side 142 of the force transmitting element 14 is provided to be a shape which is matched with the receiving body 11, so that the vaginal contractility can be substantially and basically completely inflicted to the outer side 142 of the force transmitting element 14. Preferably, the operating side 141 of the force transmitting element 14 is provided to be a shape which is matched with the inductive sides 1212 of the thin film pressure sensors 121, so that the vaginal contractility can be smoothly transmitted to the thin film pressure sensors 121 and inducted and detected effectively by the thin film pressure sensors 121.

Referring to FIG. 5 to FIG. 12 of the drawings, the detector 10 further comprise a coat 15, wherein the coat 15 has an operating room 1501, wherein the receiving body 11 is provided within the operating room 1501, wherein the coat 15 has an inner wall 151, wherein every force transmitting element 14 is provided between the thin film pressure sensors and the inner wall 151 of the coat 15. Preferably, the force transmitting element 14 is provided to be a shape which is matched with the inner wall 151 of the coat 15, so that the vaginal contractility can be able to be transmitted naturally and smoothly to the thin film pressure sensors 121. More preferably, the force transmitting element 14 is provided within the inner wall 151 of the coat 15 in the form of integral. In other words, every force transmitting element 14 is protruded from the inner wall 151 of the coat 15.

It is worth noting that the coat 15 is made of one or more materials which are friendly to human beings, for example, it is made of the silicone materials which are belong to pharmaceutical grade. As known as the person skilled in the art, the coat 15 is also made of the other human friendly materials, for example the rubber material which is belong to pharmaceutical grade.

Referring to FIG. 6 to FIG. 12 of the drawings, the receiving body 11 of the detector 10 further has a plurality of protecting grooves 113, wherein the protecting grooves 131 are respectively provided on the outer wall 111 of the receiving body 11, and the pressure detector 12 further comprise a plurality of connecting elements 122, wherein the every protecting groove 113 extends between the two installing positions 112 and the every connecting element 122 is provided between the two thin film pressure sensors 121 in the form of integral, wherein the connecting elements 122 are respectively provided on the protecting grooves 113 of the receiving body 11.

Referring to FIG. 5 to FIG. 11 of the drawings, the data processing unit 13 of the detector 10 further comprises a signal transforming module 132, wherein the signal transforming module 132 is connected electrically with the pressure detector 12 and the first communicating module 131 respectively, wherein the signal transforming module 132 is capable of receiving the real-time detecting signal from the pressure detector 12 and it can make the real-time detecting signal be transformed from the analog electronic signal into the figure signal, wherein the first communicating module 131 is capable of receiving the real-time detecting signal from the signal transforming module 132 and transmitting the real-time detecting signal to the receiver. Therefore, the first communicating module 131 is generally capable of transmitting the figure signal. Furthermore, the signal transforming module 132 is connected electrically with the thin film pressure sensors 121 of the pressure detector 12 respectively, so that it can make the real-time detecting signal from the thin film pressure sensor 121 of the pressure detector 12 to be transmitted from the analog electronic signal into the figure signal.

Referring to FIG. 5 to FIG. 12 of the drawings, the data processing unit 13 of the detector 10 further comprises a signal amplifying module 133, wherein the signal amplifying module 133 is connected electrically with the signal transforming module 132 and the pressure detector 12 respectively, wherein the signal amplifying module 133 is provided to amplify the detecting signal from the thin film pressure sensor 121 of the pressure detector 12.

Referring to FIG. 5 to FIG. 12 of the drawings, the detector 10 further comprises a power managing module 16, wherein the power managing module 16 is connected electrically with the pressure detector 12 and the data processing unit 13 of the detector 10 respectively to supply the power, wherein the power managing module 16 generally comprises an electrical energy storage device 161, such as energy storage battery. With the development of the semiconductor technology, the power managing module 16 can have a wireless power supply circuit (or wire circuit) for supplying the power to the pressure detector 12 and the data processing unit 13 of the detector 10, as known as the person skilled in the art. Therefore, the pressure detector 12 and the data processing unit 13 of the detector 10 are powered through the wireless power supply circuit (or wire circuit) of the power managing module 16. Although the power managing module 16 has its own power supply, such as the electrical energy storage device 161, the power managing module 16 is likely to have a wireless power supply circuit (or wire circuit) for charging for the electrical energy storage device 161 (if the battery is rechargeable battery). For example, the rechargeable battery of the power managing module 16 can be charged through the wireless power supply circuit (or wire circuit), as known as the person skilled in the art. Preferably, the power managing module 16 further comprises a switching module 162, wherein the switching module 162 can control the power supply which is supplied by the power managing module 16 to the pressure detector 12 and the data processing unit 13, for example, the switching module 162 is capable of controlling the power supply which is provided through the power managing module 16 for the thin film pressure sensor 121, the first communicating module 131, the signal transforming module 132 and the signal amplifying module 133 of the data processing unit 13 and/or an indicator.

It should be noticed that the data transmitted between the data processing unit 13 of the detector 10 and the receiver such as the processor 20 can be realized through an electronic communicating network. The electronic communicating network can be a local area network, a metropolitan area network, a wide area network, a network such as internet, Wi-Fi, or locally communicating connection, such as USB, PCI and so on. The data transmitted between the data processing unit 13 of the detector 10 can also be connected through the local network, such as it is realized through the Bluetooth communicator. The electronic communicating network can be a mobile communicating network, such as GSM network, CDMA network, TD-CDMA network, 3Gnetwork, 4Gnetwork, and other data transmitting means as known as the person skilled in the art. The receiver may be an electronic device which can display or visualize the detecting data from the detector 10, such as computer, laptop, smartphone, tablet PC and so on. The receiver can be computerized or programmed to process the real-time detecting data and/or make the real-time detecting data visualization, so that the user can understand the results represented by the real-time detecting data. The receiver may also comprise a displayer for displaying the detecting data which is processed.

Referring to FIG. 5 to FIG. 12 of the drawings, the detector 10 further comprises a lid 17, wherein the lid 17 can seal the receiving chamber 110 of the receiving body 11 and hermetically make the pressure detector 12 within the operating room 1501 of the coat 15.

Referring to FIG. 5 to FIG. 12 of the drawings, the detector 10 further comprises a pulling element 18, wherein the pulling element 18 is provided on the lid 17 for helping the user to pull the detector 10 from the user's vagina. In some embodiments, the pulling element 18 is provided within the receiving body 11 or the coat 15.

Referring to FIG. 5 to FIG. 12 of the drawings, the processor 20 comprises a data processing module 21 and a second communicating module 22 connected electrically to the data processing module 21, wherein the second communicating module 22 is capable of receiving the real-time detecting signal transmitted by the data processing unit 13 of the detector 10, and transmitting the real-time detecting signal to the data processing module 21. In other words, the first communicating module 131 of the data processing unit 13 of the detector 10 connects electrically to the data processing module 21 of the processor 20, wherein the first communicating module 131 of the data processing unit 13 is capable of receiving the real-time detecting data from the pressure detector 12 of the detector 10, and sending the real-time detecting data to the second communicating module 22 of the processor 20, wherein the second communicating module 22 is provided to be connected electrically with the first communicating module 131 of the data processing unit 13, so that the second communicating module 22 can receive the detecting data from the first communicating module 131, and send the detecting data to the data processing module 21 of the processor 20. Preferably, the processor 20 is capable of receiving the detecting data from the data processing unit 13 of the detector 10 and process the detecting data to generate an understandable data, wherein the understandable data can be visually displayed and known by the user. Furthermore, the data processing module 21 of the processor 20 is capable of receiving the detecting data from the first communicating module 131 of the data processing unit 13 through the second communicating module 22, and sending the detecting data to the data processing module 21 of the processor 20, wherein the data processing module 21 is capable of receiving the detecting data from the data processing unit 13 of the detector 10 and process the detecting data to generate an understandable data, wherein the understandable data can be visually displayed and known by the user.

The processor 20 is capable of calculating the vaginal contractility of the user (F) by the following formulas:

$$Fs-b=-(VT*RF)/(a*Vout);$$

$$F=Fs-Fc;$$

Wherein the Vout is measuring voltage, VT is the voltage loaded into the thin film pressure sensor 121, RF is the resistance of the signal amplifying module 133 (if any), a and b are the characteristic constants of the thin film pressure sensor 121, Fc is the pressure detected by thin film pressure sensor 121 of the detector 10 in the case of the coat 15 of the detector 10 is not imposed pressure. Understandably, the pressure Fc is the pressure which is imposed by the coat 15 of the detector 10 to the thin film pressure sensor 121 of the detector 10. Therefore, the pressure Fc should be removed when calculate the actually vaginal contractility F of the user. Preferably, the value range of a is [1,100000], the value range of b is [0.1,100].

Referring to FIG. 5 to FIG. 12 of the drawings, the physical training system for pelvic floor muscle according to the preferred embodiment of the present invention further comprises a Client 30, wherein the Client 30 can display the real-time detecting data which is visually processed by the processor 20 to make the real-time detecting data be sensed by the user. Preferably, the Client 30 and the processor 20 are connected electrically with each other. More preferably, the Client 30 and the processor 20 are integrated together and forms a portable device.

The present invention further provides a detector 10 used to detect the contractility of the vaginal inner wall of the user according to the preferred embodiment of the present invention, wherein the detector 10 comprises an receiving body 11, a pressure detector 12 and a data processing unit 13, wherein the receiving body 11 defines a receiving chamber 110, the pressure detector 12 is provided within the imbedding room 11, the data processing unit 13 is provided within the receiving chamber 110, wherein the pressure detector 12 is provided to detect the pressure which is put on by the vaginal inner wall and generates a real-time detecting signal, the data processing unit 13 is capable of receiving the real-time detecting signal from the pressure detector 12 and transmit the real-time detecting signal to a receiver, such as the above processor 20. The data processing unit 13 is generally capable of transmitting figure signal. As known as the person skilled in the art, the data processing unit 13 is also set to transmit the analog electronic signal. Therefore, the real-time detecting signal can be transmitted by the data processing unit 13, and the real-time detecting signal can be analog electronic signal or figure signal.

Referring to FIG. 5 to FIG. 12 of the drawings, the data processing unit 13 of the detector of the physical training system for pelvic floor muscle according to the above preferred embodiment of the present invention comprises a first communicating module 131, wherein the first communicating module 131 of the data processing unit 13 is capable of receiving the real-time detecting signal from the pressure detector 12 and transmit the real-time detecting signal to the processor 20. The first communicating module 131 is generally set to transmit the figure signal. As known as the person skilled in the art, the first communicating module 131 is also set to transmit the analog electronic signal. Therefore, the real-time detecting signal can be transmitted by the first communicating module 131, and the real-time detecting signal can be analog electronic signal or figure signal.

Referring to FIG. 6 to FIG. 8 of the drawings, the pressure detector 12 of the detector comprises a plurality of thin film pressure sensor 121, wherein every thin film pressure sensor 121 of the pressure detector 12 is connected electrically with the data processing unit 13. Preferably, every thin film pressure sensor 121 of the pressure detector 12 which is also connected with each other in series is connected electrically with the data processing unit 13. As known as the person skilled in the art, the data processing unit 13 can receive the contractility detecting signal of the vaginal inner wall from the thin film pressure sensor 121 of the pressure detector 12. Furthermore, the thin film pressure sensors 121 of the pressure detector 12 are all connected electrically with the first communicating module 131 of the data processing unit 13. Therefore, the thin film pressure sensor 121 of the pressure detector 12 which are connected in parallel are connected electrically with the first communicating module 131 of the data processing unit 13.

Referring to FIG. 6 to FIG. 12 of the drawings, the receiving body 11 of the detector 10 has a plurality of outer walls 111 and comprises an installing position 112 provided on the outer walls 111 of the receiving body 11, wherein every outer wall 111 has an installing surface 1120, wherein the thin film pressure sensors 121 of the pressure detector 12 is adopted to provided on the installing surface 1120.

It is worth noting that the thin film pressure sensor 121 preferably has an installing side 1211 and an inductive side 1212, wherein the installing side 1211 is provided on the installing position 112 of the receiving body 11, wherein the contractility from the vagina can be directly or indirectly presses on the inductive side 1212 of the thin film pressure sensor 121.

Referring to FIG. 6 to FIG. 12 of the drawings, the detector 10 further comprises a plurality of force transmitting elements 14, wherein the force transmitting elements 14 are respectively provided on the thin film pressure sensor 121 of the pressure detector 12, where the every force transmitting element 14 has an operating side 141 and an outer side 142, wherein the operating side 141 of the force transmitting element 14 is pressed on the thin film pressure sensors 121, wherein the outer side 142 of the force transmitting element 14 is provided to be a shape which is matched with the receiving body 11, so that the vaginal contractility can be substantially and basically completely inflicted to the outer side 142 of the force transmitting element 14. Preferably, the operating side 141 of the force transmitting element 14 is provided to be a shape which is matched with the inductive sides 1212 of the thin film pressure sensors 121, so that the vaginal contractility can be smoothly transmitted to the thin film pressure sensors 121 and inducted and detected effectively by the thin film pressure sensors 121.

Referring to FIG. 5 to FIG. 12 of the drawings, the detector 10 further comprise a coat 15, wherein the coat 15 has an operating room 1501, wherein the receiving body 11 is provided within the operating room 1501, wherein the coat 15 has an inner wall 151, wherein every force transmitting element 14 is provided between the thin film pressure sensors and the inner walls 151 of the coat 15. Preferably, the force transmitting element 14 is provided to be a shape which is matched with the inner wall 151 of the coat 15, so that the vaginal contractility can be able to be transmitted naturally and smoothly to the thin film pressure sensor 121. More preferably, the force transmitting element 14 is provided within the inner wall 151 of the coat 15 in the form of integral. In other words, every force transmitting element 14 is protruded from the inner wall 151 of the coat 15.

It is worth noting that the coat 15 is made of one or more materials which are friendly to human beings, for example, it is made of the silicone materials which are belong to pharmaceutical grade. As known as the person skilled in the art, the coat 15 is also made of the other human friendly materials, for example the rubber material which is belong to pharmaceutical grade.

Referring to FIG. 6 to FIG. 12 of the drawings, the receiving body 11 of the detector 10 further has a plurality of protecting grooves 113, wherein the protecting grooves 131 are respectively provided on the outer wall 111 of the receiving body 11, and the pressure detector 12 further comprise a plurality of connecting elements 122, wherein the every protecting groove 113 extends between the two installing positions 112 and the every connecting element 122 is provided between the two thin film pressure sensors 121 in the form of integral, wherein the connecting elements 122 are respectively provided on the protecting grooves 113 of the receiving body 11.

Referring to FIG. 5 to FIG. 11 of the drawings, the data processing unit 13 of the detector 10 further comprises a signal transforming module 132, wherein the signal transforming module 132 is connected electrically with the pressure detector 12 and the first communicating module 131 respectively, wherein the signal transforming module 132 is capable of receiving the real-time detecting signal from the pressure detector 12 and it can make the real-time detecting signal to be transmitted from the analog electronic signal into the figure signal, wherein the first communicating module 131 is capable of receiving the real-time detecting signal from the signal transforming module 132 and transmit the real-time detecting signal to the receiver. Therefore, the first communicating module 131 is generally capable of transmitting the figure signal. Furthermore, the signal transforming module 132 is connected electrically with the thin film pressure sensors 121 of the pressure detector 12 respectively, so that it can make the real-time detecting signal from the thin film pressure sensor 121 of the pressure detector 12 to be transmitted from the analog electronic signal into the figure signal, Referring to FIG. 5 to FIG. 12 of the drawings, the data processing unit 13 of the detector 10 further comprises a signal amplifying module 133, wherein the signal amplifying module 133 is connected electrically with the signal transforming module 132 and the pressure detector 12 respectively, wherein the signal amplifying module 133 is provided to amplify the detecting signal from the thin film pressure sensor 121 of the pressure detector 12.

It is worth noting that the processor 20 is capable of calculating the vaginal contractility of the user (F) by the following formulas:

$$Fs-b=-(VT*RF)/(a*Vout);$$

$$F=Fs-Fc; (F \text{ is final pressure})$$

Wherein the Vout is measuring voltage, VT is the voltage loaded into the thin film pressure sensor 121, RF is the resistance of the signal amplifying module 133 (if any), a and b are the characteristic constants of the thin film pressure sensor 121, Fc is the pressure detected by thin film pressure sensor 121 of the detector 10 in the case of the coat 15 of the detector 10 is not imposed pressure. Understandably, the pressure Fc is the pressure which is imposed by the coat 15 of the detector 10 to the thin film pressure sensor 121 of the detector 10. Therefore, the pressure Fc should be removed when calculate the actually vaginal contractility F of the user. Preferably, the value range of a is [1,100000], the value range of b is [0.1,100].

Referring to FIG. 5 to FIG. 12 of the drawings, the detector 10 further comprises a power managing module 16, wherein the power managing module 16 is connected electrically with the pressure detector 12 and the data processing unit 13 of the detector 10 respectively to supply the power, wherein the power managing module 16 generally comprises an electrical energy storage device 161, such as energy storage battery. With the development of the semiconductor technology, the power managing module 16 can have a wireless power supply circuit (or wire circuit) for supplying the power to the pressure detector 12 and the data processing unit 13 of the detector 10, as known as the person skilled in the art. Therefore, the pressure detector 12 and the data processing unit 13 of the detector 10 are powered through the wireless power supply circuit (or wire circuit) of the power managing module 16. Although the power managing module 16 has its own power supply, such as the electrical energy storage device 161, the power managing module 16 is likely to have a wireless power supply circuit (or wire circuit) for charging for the electrical energy storage device 161 (if the battery is rechargeable battery). For example, the rechargeable battery of the power managing module 16 can be charged through the wireless power supply circuit (or wire circuit), as known as the person skilled in the art. Preferably, the power managing module 16 further comprises a switching module 162, wherein the switching module 162 can control the power supply which is supplied by the power managing module 16 to the pressure detector 12 and the data processing unit 13, for example, the switching module 162 is capable of controlling the power supply which is provided through the power managing module 16 for the thin film pressure sensor 121, the first communicating module 131, the signal transforming module 132 and the signal amplifying module 133 of the data processing unit 13 and/or an indicator.

Electively, the processor 20 is connected electrically to the data processing unit 13 of the detector 10 to make the data processing unit 13 of the detector 10 be able to transmit the real-time detecting data to the processor 20. Therefore, the processor 20 can be further provided onto the receiving chamber 110 of the receiving body 11.

Figure 13:
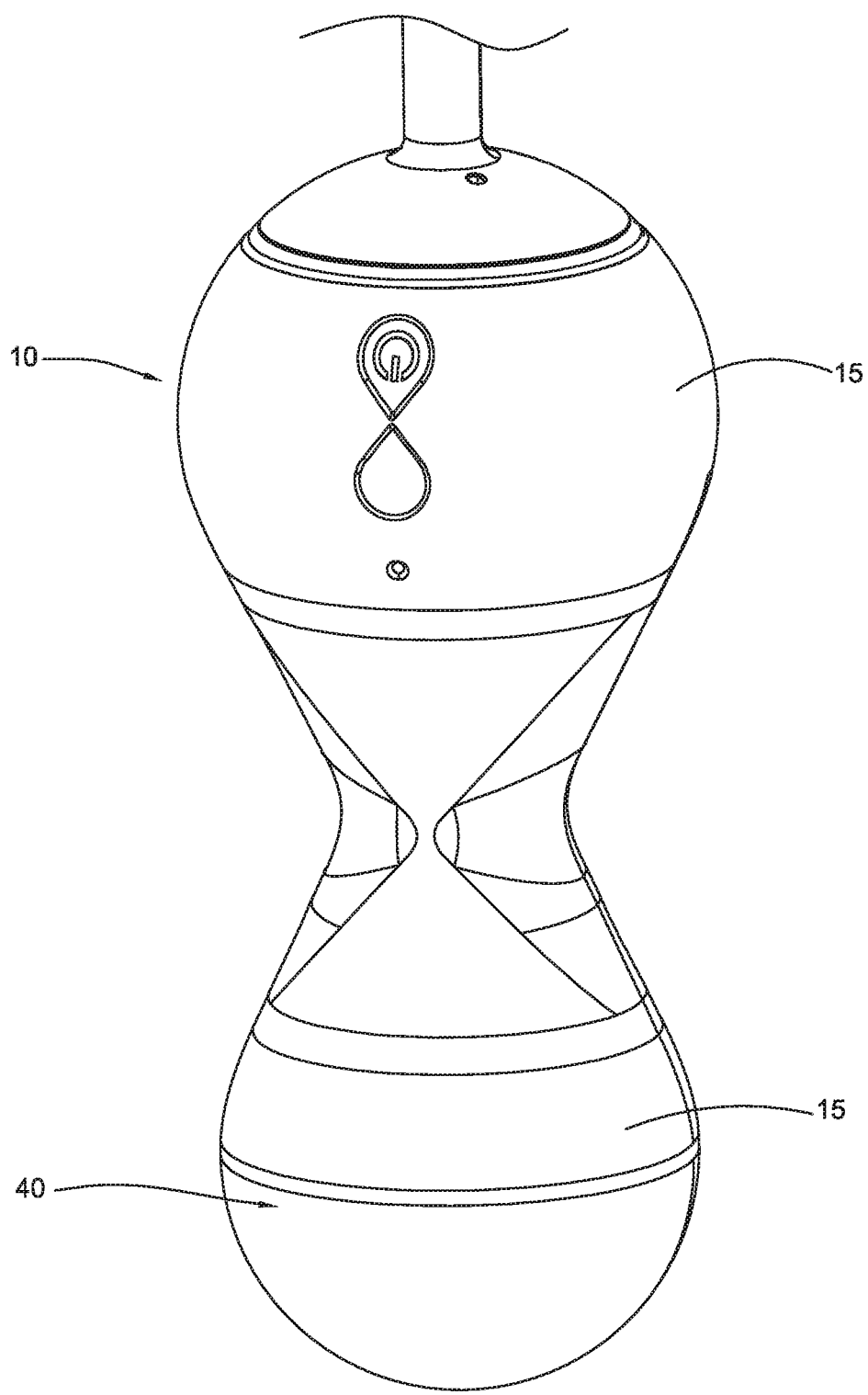
FIG. 13 is a perspective view of the detector of the physical training system for pelvic floor muscle according to the above preferred embodiment of the present invention.
Figure 14:
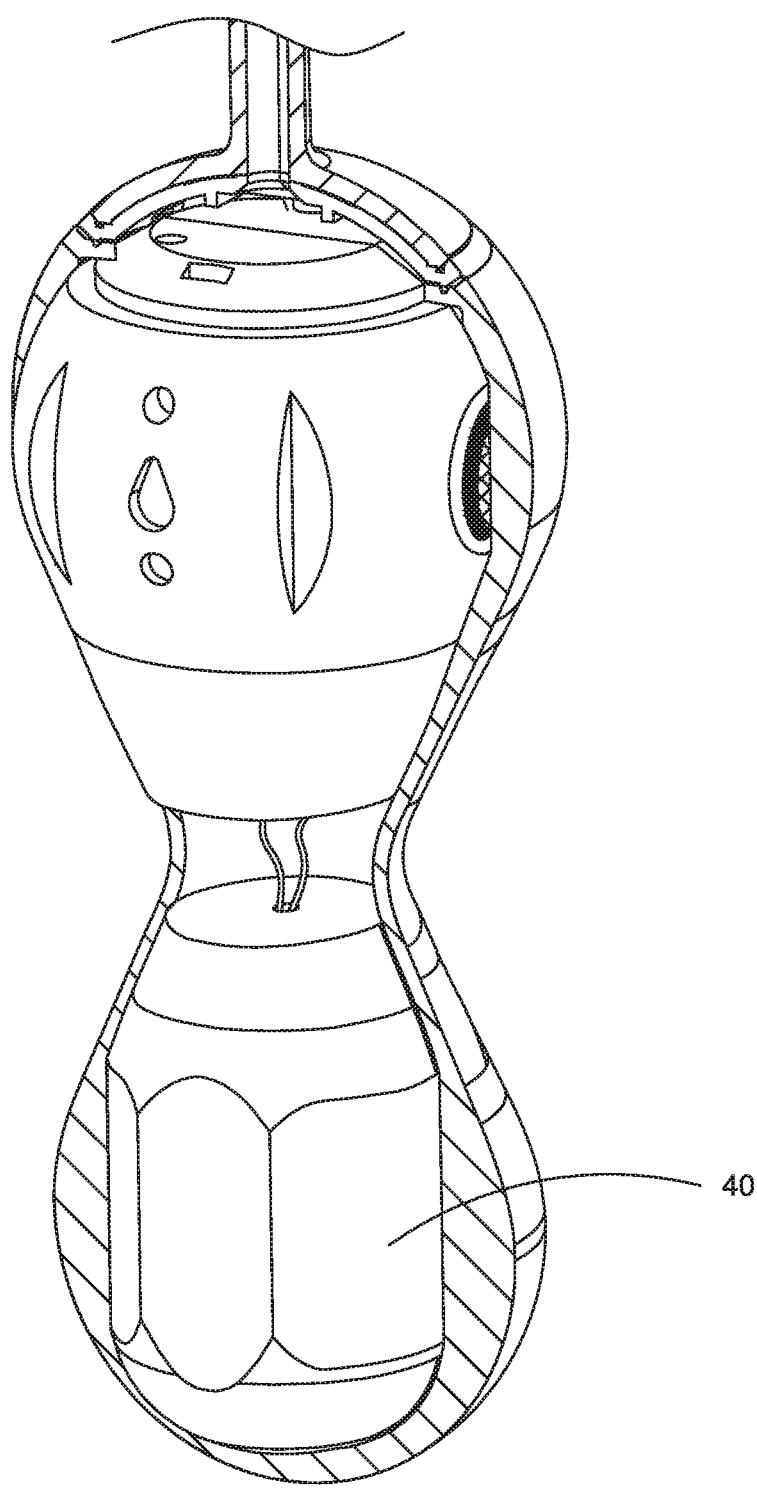
FIG. 14 is a sectional view of the detector of the physical training system for pelvic floor muscle according to the above preferred embodiment of the present invention.

Referring to FIG. 13 and FIG. 14 of the drawings, the physical training system for pelvic floor muscle further comprises a stimulator 40, wherein the stimulator 40 is adopted to be provided within the user's body, wherein the stimulator 40 is connected electrically with the power managing module 16 of the detector 10, in order to make the power managing module 16 supply the power to the stimulator 40, so that the stimulator 40 can provide a stimulation which can be felt by the vagina to the user for helping the exerciser to exercise the pelvic floor muscle. Preferably, the stimulator 40 is a vibrator.

Referring to FIG. 13 and FIG. 14 of the drawings, the coat 15 of the detector 10 of the physical training system for pelvic floor muscle further forms a vibrating room 1502, wherein the stimulator 40 is provided within the vibrating room 1502. Understandably, the coat 15 can be glued to the coat 15, so that the stimulating movement will be transmitted by the coat 15 when the stimulator 40 generates a stimulating movement, so when the stimulator 40 and the receiving body 11 of the detector 10 are put into the exerciser's body and providing the electricity to the stimulator 40, the stimulator 40 will be activated and provide a stimulation which can be felt by vaginal inner wall. Preferably, the stimulator 40 is connected electrically to the data processing unit 13 of the detector 10, so that the data processing unit 13 of the detector 10 can send order to the stimulator 40 and control the stimulating production mode of the stimulator 40.

Figure 15:
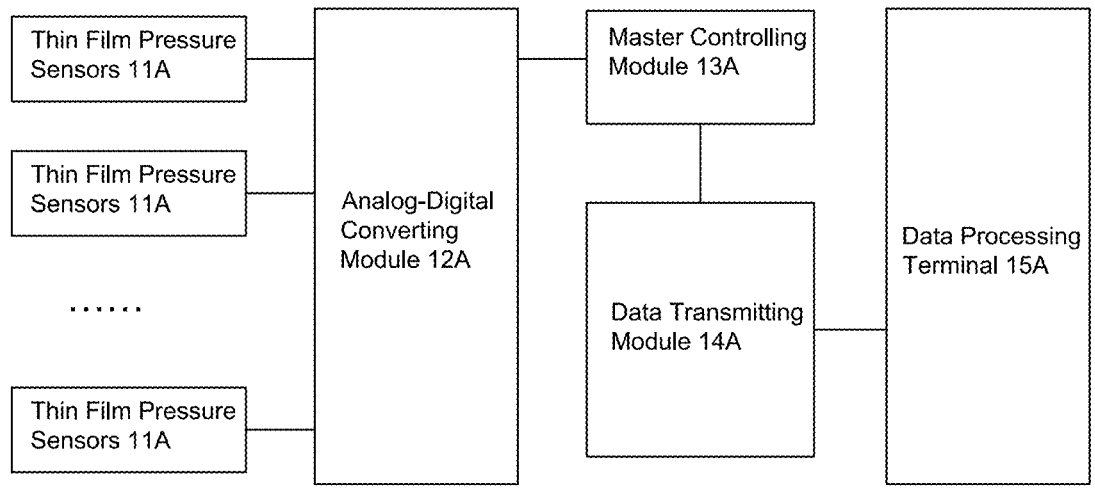
FIG. 15 is a schematic diagram of circuit of the voltage amplification circuit of one optional embodiment of the detector of the physical training system for pelvic floor muscle according to the above preferred embodiment of the present invention.

Referring to FIG. 15 of the drawings, an optional embodiment of the detector 10 of the physical training system for pelvic floor muscle according to the preferred embodiment of the present invention will be illuminated, wherein the detector 10A is adopted to detect the pressure of the female's pelvic floor muscle through detecting the pressure inside the female's vagina, which comprises a plurality of thin film pressure sensors 11A, an analog-digital converting module 12A, a master controlling module 13A, a data transmitting module 14A and a data processing terminal 15A.

There is many thin film pressure sensors 11A, a plurality of thin film pressure sensors 11A are respectively arranged on the surfaces around the detecting carrier, and the surface of the thin film pressure sensor 11A is covered with medical silica gel layer, which is safe and comfortable, and easy to be cleaned.

Every thin film pressure sensor 11A is respectively connected with the voltage amplifying circuit and the analog-digital converting module 12A.

Figure 16:
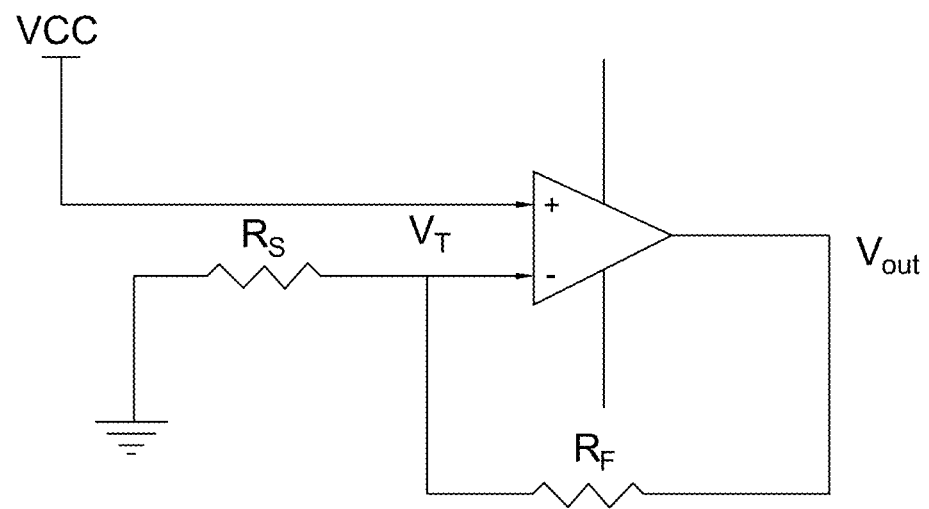
FIG. 16 is a schematic diagram of circuit one optional embodiment of the detector of the physical training system for pelvic floor muscle according to the above preferred embodiment of the present invention.

The voltage amplifying circuit is shown as the FIG. 16.

Wherein the detecting carrier (the wearable product) is used to carry the thin film pressure sensor 11A into the human body.

The present invention employs a plurality of thin film pressure sensors, which has many advantages, such as small volume, high sensitivity, more contracting points with human body, which can detect multiple points, which improves the precision of detecting and reduces the volume of the device, so that the design of which is suitable to the wearable product.

The analog-digital converting module 12A connects to the above voltage amplifying circuit, in order to convert the measuring voltage which is output through the voltage amplifying circuit to the digital signal of the measuring voltage.

The master controlling module 13A connects to the analog-digital converting module 12A, in order to obtain the digital signal of the measuring voltage from the analog-digital converting module 12A, the master controlling module 13A can calculate the pressure values imposed to the thin film pressure sensor 11A through the formulas (1) and (2), and control the data transmitting module 14A send the voltage values to the data processing terminal 15A:

$$V\text{out}=-VT*(RF/RS) \quad (1)$$

Wherein the Vout is the measuring voltage, the VT is the reference voltage loaded into the thin film pressure sensor 11A, the RF is the reference resistance of the amplifying circuit, the RS is the resistance of the thin film pressure sensor 11A.

Because of the thin film pressure sensor 11A can be equivalent to voltage dependent resistor, the resistance RS can be calculated through the formula (1).

The circuit is in a high impedance state when the thin film pressure sensor 11A doesn't have the external load. When the external pressure is imposed to the thin film pressure sensor 11A, the resistance of the circuit drops, the pressure and the resistance is in a state of inverse ratio, so the pressure values applied on the thin film pressure sensor 11A can be calculated through the formula (2).

$$RS=a*F-b \quad (2)$$

Wherein the F is the pressure value loaded into the thin pressure sensor 11A, a and b are the characteristic constants of the thin film pressure sensor 11A, which can be obtained through mathematical fit and regression analysis of the thin film pressure sensor 11A. The above factors may be difference due to the difference of the acreage, technology of the thin film pressure sensor 11A, they can have different values depending on the difference of the measuring force and sensitivity. The value range of a is [1,100000], the value range of b is [0.1,100].

In order to improve the accuracy of the detecting, the master controlling module 13 can filter the noise generated in the process of the detecting through the denoise processing.

The data transmitting module 14A connects to the master controlling module 13A for making the master controlling module 13A send the pressure value to the data processing terminal 15A.

The data processing terminal 15A wired or wireless connects to the data transmitting module 14A for processing the above pressure further. Of course, the data processing terminal 15A also can be omitted, and it can be replaced by the ready-made equipment which has the function of analyzing and processing.

Wherein the data processing terminal 15A is computer, smartphone or tablet computer, the computer can connect to the data transmitting module 14A through the data line, the smartphone and the tablet computer can connect to the data transmitting module 14A through the data line, and it is also connected to the data transmitting module 14A through the wireless transmitting technology, such as Bluetooth, and now the data transmitting module 14A is a Bluetooth radio frequency chip.

Understandably, the above pressure values needn't be transmitted to the data processing terminal 15A through the data transmitting module 14A immediately, so the embodiment also designs a data storage unit which is connected with the master controlling module 13A for storing the pressure values.

Understandably, the master controlling module 13A and the data transmitting module 14A can be integrated in a single chip.

Figure 17:
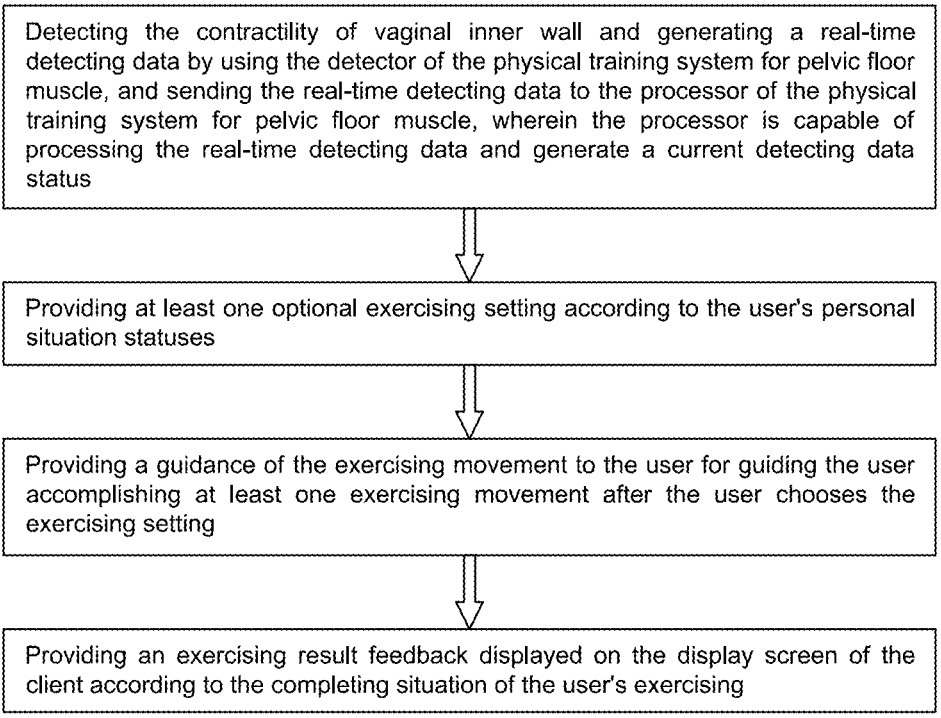
FIG. 17 is a schematic flow diagram for guiding the exercisers to exercise according to the above preferred embodiment of the present invention.

Referring to FIG. 17 of the drawings, the present invention further provides a method of guiding exerciser to exercise pelvic floor muscle, which comprises the following steps:

(a) providing at least one optional exercising setting according to the user's personal situation;

(b) providing a guidance of the exercising movement to the user for guiding the user accomplishing at least one exercising movement after the user chooses the exercising setting;

The exercising setting 101 is selected from one group of exercising settings 100, wherein the group of exercising settings 100 comprises but it is not limited to an exercising movement setting 1011, an exercising time setting 1012, an exercising intensity setting 1013, an exercising frequency setting 1014, an exercising guidance setting 1015, an exercising auxiliary setting 1016 and an exercising feedback setting 1017. The personal situation 201 is selected from a combination of personal situations 200, wherein the combination of personal situations 200 comprises but not limit to an age status 2011, a historical data status 2012, a current detecting data status 2013 and an exercising purpose status 2014.

Referring to FIG. 17 of the drawings, the method of guiding exerciser to exercise pelvic floor muscle further comprises the following step:

(a1) detecting the contractility of vaginal inner wall and generating a real-time detecting data by using the detector of the physical training system for pelvic floor muscle, and sending the real-time detecting data to the processor of the physical training system for pelvic floor muscle, wherein the processor is capable of processing the real-time detecting data and generate a current detecting data status, wherein the step (a1) is located before the step (a).

Referring to FIG. 17 of the drawings, the method of guiding exerciser to exercise pelvic floor muscle further comprises the following step:

(c) providing an exercising result feedback displayed on the display screen of the Client according to the completing situation of the user's exercising, wherein the step (c) is located after the step (b).

Figure 18:
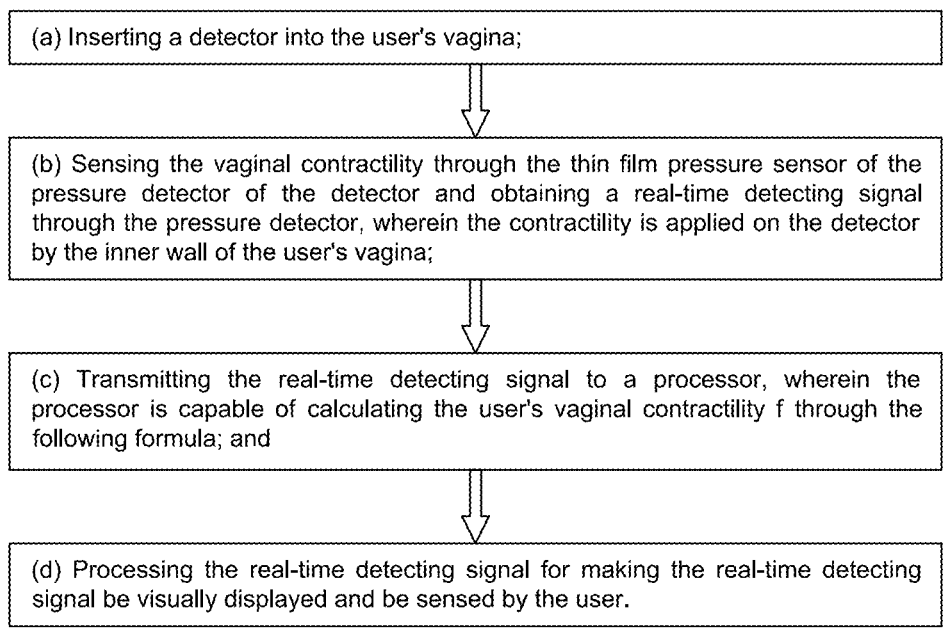
FIG. 18 is a schematic flow diagram of the detection method of the vaginal contractility according to the above preferred embodiment of the present invention.

Referring to FIG. 18 of the drawings, the present invention further provides a method of detecting vaginal contractility, which comprises the following steps:

(a) inserting a detector into the user's vagina;

(b) sensing the vaginal contractility through the thin film pressure sensor of the pressure detector of the detector and obtaining a real-time detecting signal through the pressure detector, wherein the contractility is applied on the detector by the inner wall of the user's vagina; and (c) transmitting the real-time detecting signal to a processor, wherein the processor is capable of calculating the user's vaginal contractility F through the following formula:

$$Fs-b=-(VT*RF)/(a*Vout);$$

$$F=Fs-Fc; (F \text{ is final pressure})$$

Wherein the Vout is measuring voltage, VT is the voltage loaded into the thin film pressure sensor 121, RF is the resistance of the signal amplifying module 133 (if any), a and b are the characteristic constants of the thin film pressure sensor 121, Fc is the pressure detected by thin film pressure sensor 121 of the detector 10 in the case of the coat 15 of the detector 10 is not imposed pressure. Understandably, the pressure Fc is the pressure which is imposed by the coat 15 of the detector 10 to the thin film pressure sensor 121 of the detector 10. Therefore, the pressure Fc should be removed when calculate the actually vaginal contractility F of the user. Preferably, the value range of a is [1,100000], the value range of b is [0.1,100].

Referring to FIG. 18 of the drawings, the method of detecting vaginal contractility of the present invention further comprises the following step:

(d) processing the real-time detecting signal for making the real-time detecting signal be visually displayed and be sensed by the user.

TYPICAL EXAMPLES

First Segment: The Characterization of the Product of the Typical Examples

1. Material of the coat: silicone of the pharmaceutical grade;

2. Stand-by time: the stand-by time is 180 days, the continuous using time is 4 hours in the working mode;

3. Wireless communication: Bluetooth 4.0;

4. Wireless connection: automatic identification of the connection;

5. Communication protocol: exclusive communication protocol;

6. Compatible system: IOS 7.0+;

7. Interface language: English, German, Spanish, French, Italian, simplified Chinese, traditional Chinese, Japanese and so on;

8. Exercising course: induction training, fresh hot mama, power of love, baby plan, sexy superman, postpartum rehabilitation;

9. Guiding mode: voice guiding (audio);

10. Feedback mode: medal reward.

Second Segment: Starting Device

The physical training system for pelvic floor muscle has two starting modes, there are hard starting and soft starting.

The user can start and activate the detector 10 of the physical training system for pelvic floor muscle through the power switching button. The user can also wirelessly start and activate the detector 10 of the physical training system for pelvic floor muscle through the input equipment of the Client 30. Now, the user input the starting instruction through the input equipment of the Client 30, the processor send the starting instruction to the data processing unit 13, the data processing unit 13 further send the starting instruction to the switching module 162 of the power managing module 16, the switching module 162 control the power managing module 16 to supply power to the pressure detector 12, the stimulator 40 and the data processing unit 13, the detector 10 and the stimulator 40 of the physical training system for pelvic floor muscle are started. If the processor 20 and the detector 10 are all provided on the receiving body 11, the switching module 162 control the power managing module 16 to further supply power to the processor 20.

The processor 20 is generally integrated together with the Client 30 to form a portable device, such as smartphone, in order to use conveniently for the user.

Third Segment: Device Setting

Figure 19:
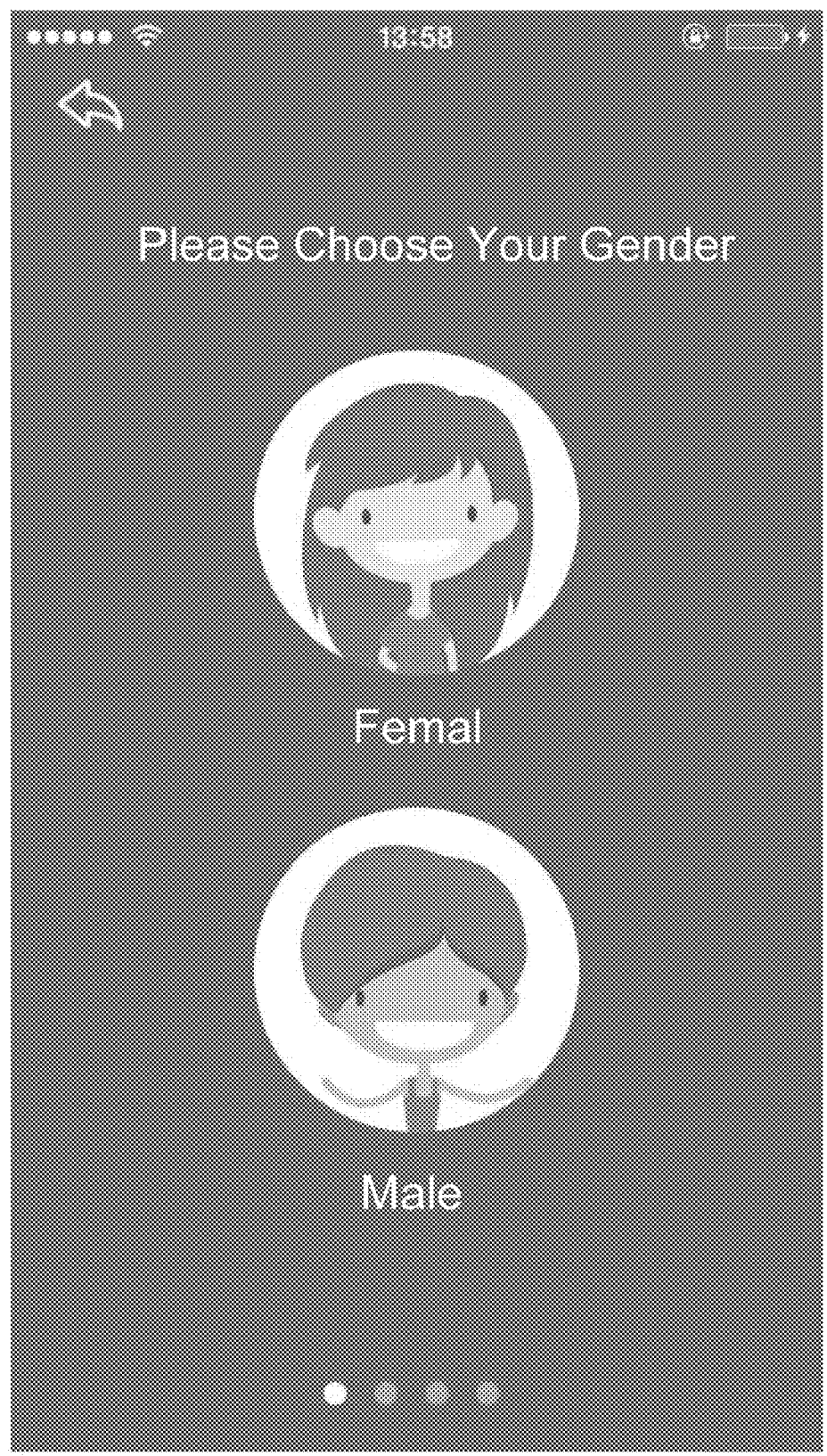
FIG. 19 is a work interface which is displayed on the display screen of the Client of the physical training system for pelvic floor muscle when the system is started according to the above preferred embodiment of the present invention.
Figure 20:
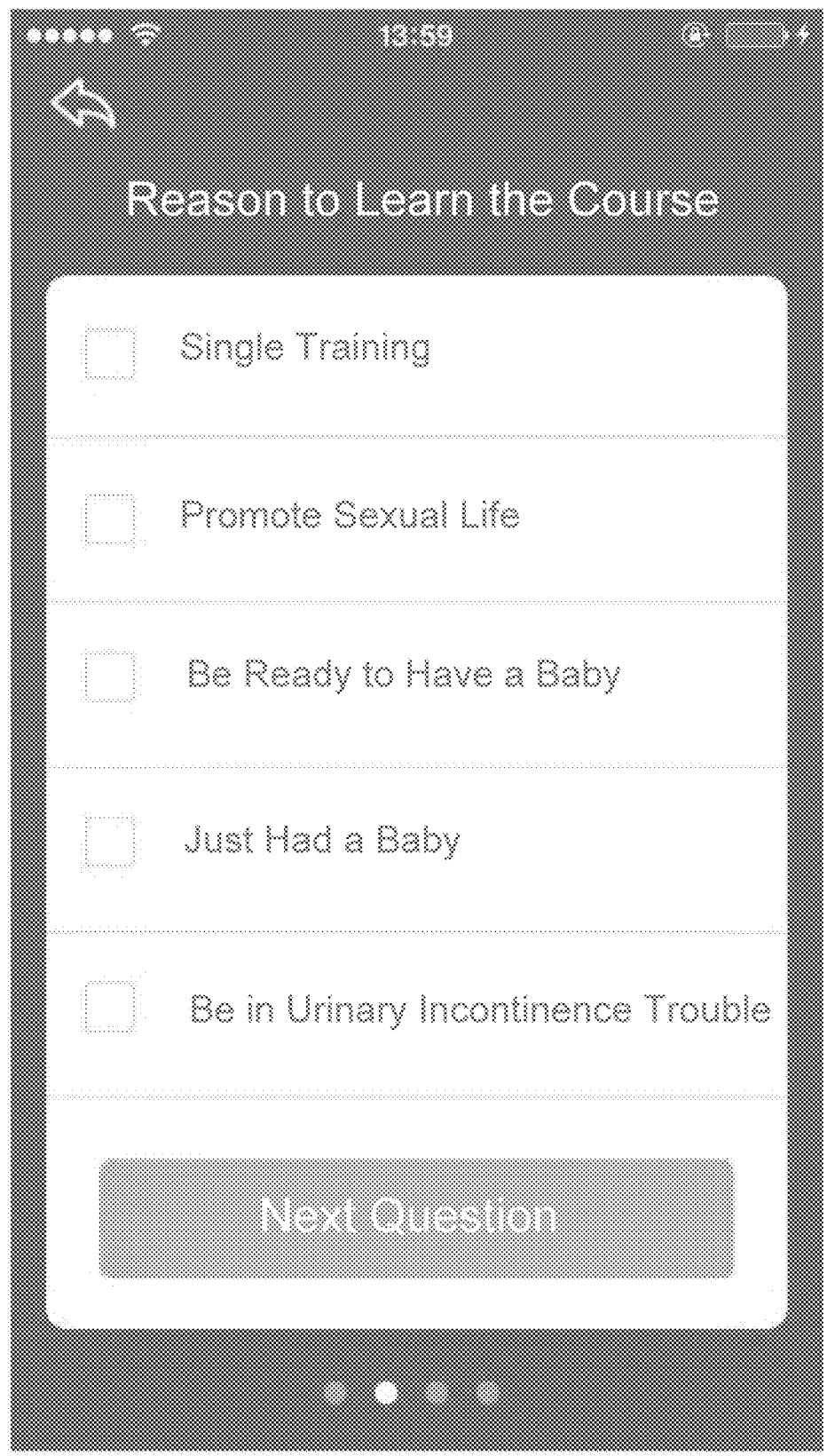
FIG. 20 is an optional interface of the exercising objective which is displayed on the display screen of the Client of the physical training system for pelvic floor muscle when the system is started according to the above preferred embodiment of the present invention.
Figure 21:
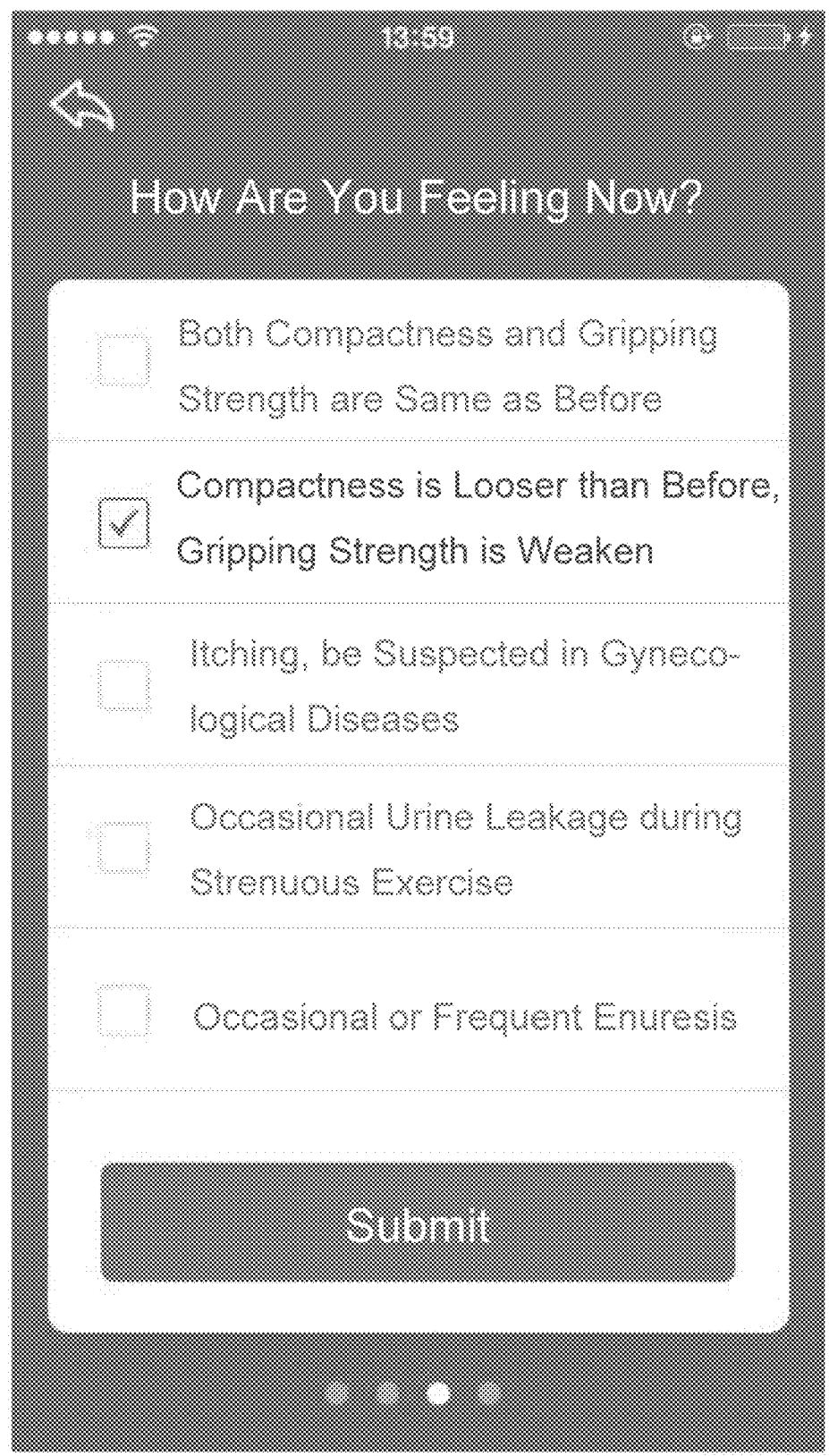
FIG. 21 is an input interface of the historical data which is displayed on the display screen of the Client of the physical training system for pelvic floor muscle when the system is started according to the above preferred embodiment of the present invention.
Figure 22:
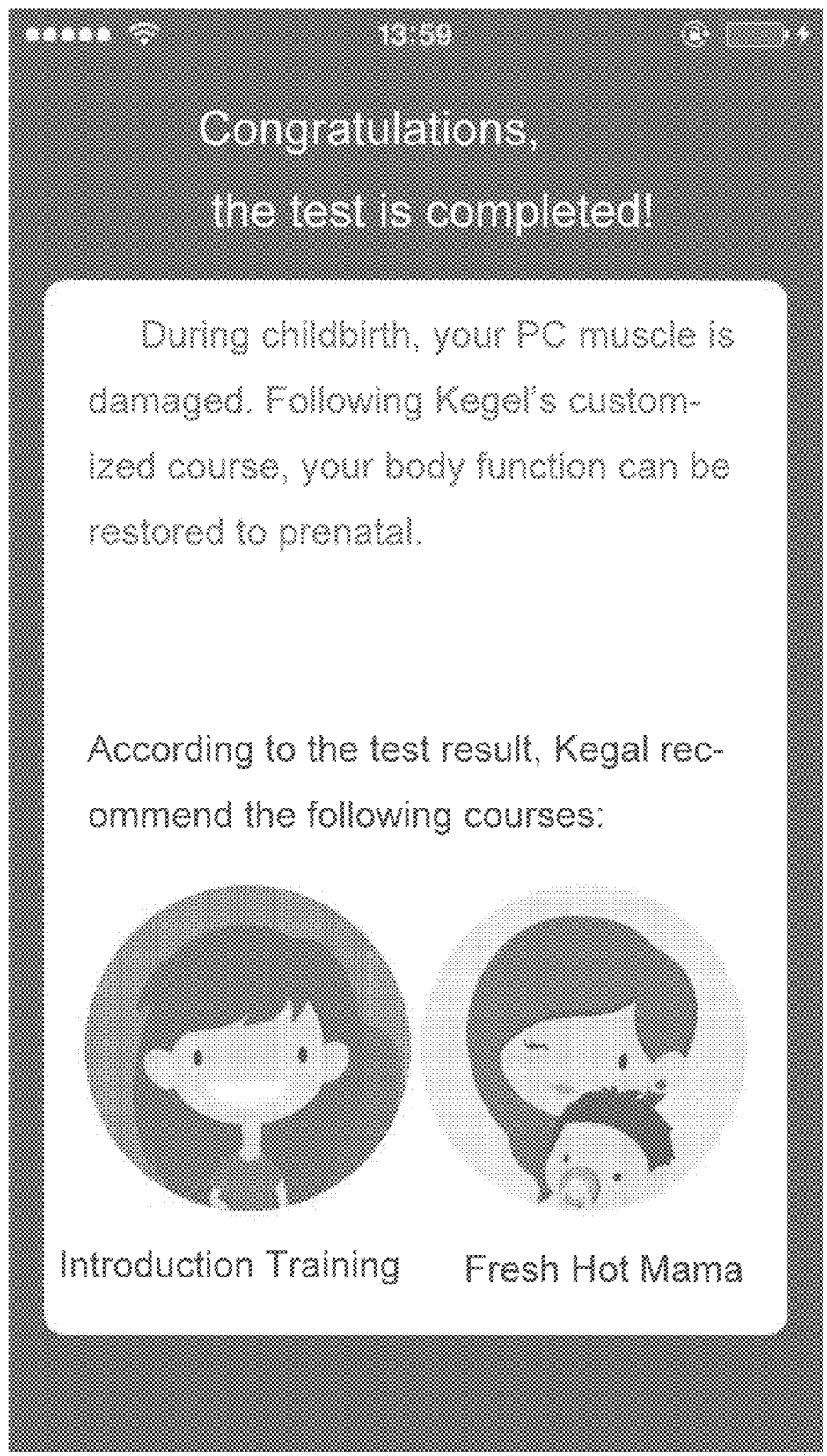
FIG. 22 is an optional interface of the suggested exercising courses which is displayed on the display screen of the Client of the physical training system for pelvic floor muscle when the system is started according to the above preferred embodiment of the present invention.

Referring to FIG. 19 of the drawings, the physical training system for pelvic floor muscle is started and provides a working interface of the display screen of the Client 30, wherein the user can input a personal situation 201 to the physical training system for pelvic floor muscle through the sexual selection interface, such as sex, or the exercising purpose status 2014 shown in FIG. 20 of the drawings, or the historical data status 2012 shown in FIG. 21 of the drawings, in order to make the physical training system for pelvic floor muscle provide at least one optional exercising setting 101 to the user, such as the optional exercising courses displayed on the display screen 31 of the Client 30 of the physical training system for pelvic floor muscle as shown in FIG. 22 of the drawings, wherein the every exercising course may be corresponding to the optional exercising settings (combination) 101 (The details can be seen in the following table 1 to table 6).

Figure 23:
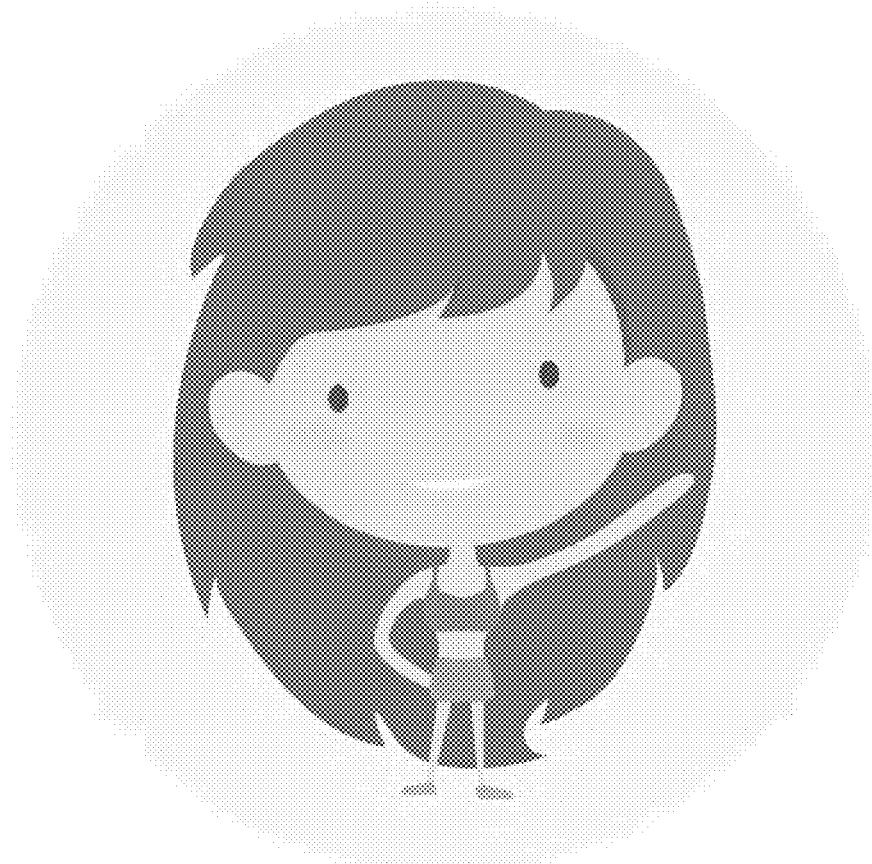
FIG. 23 is an interface when the user choose into the primary level training of the introductory training course after the physical training system for pelvic floor muscle is started according to the above preferred embodiment of the present invention.
Figure 24:
FIG. 24 is an interface when the user choose into the primary level training of the fresh hot mom's course after the physical training system for pelvic floor muscle is started according to the above preferred embodiment of the present invention.
Figure 25:
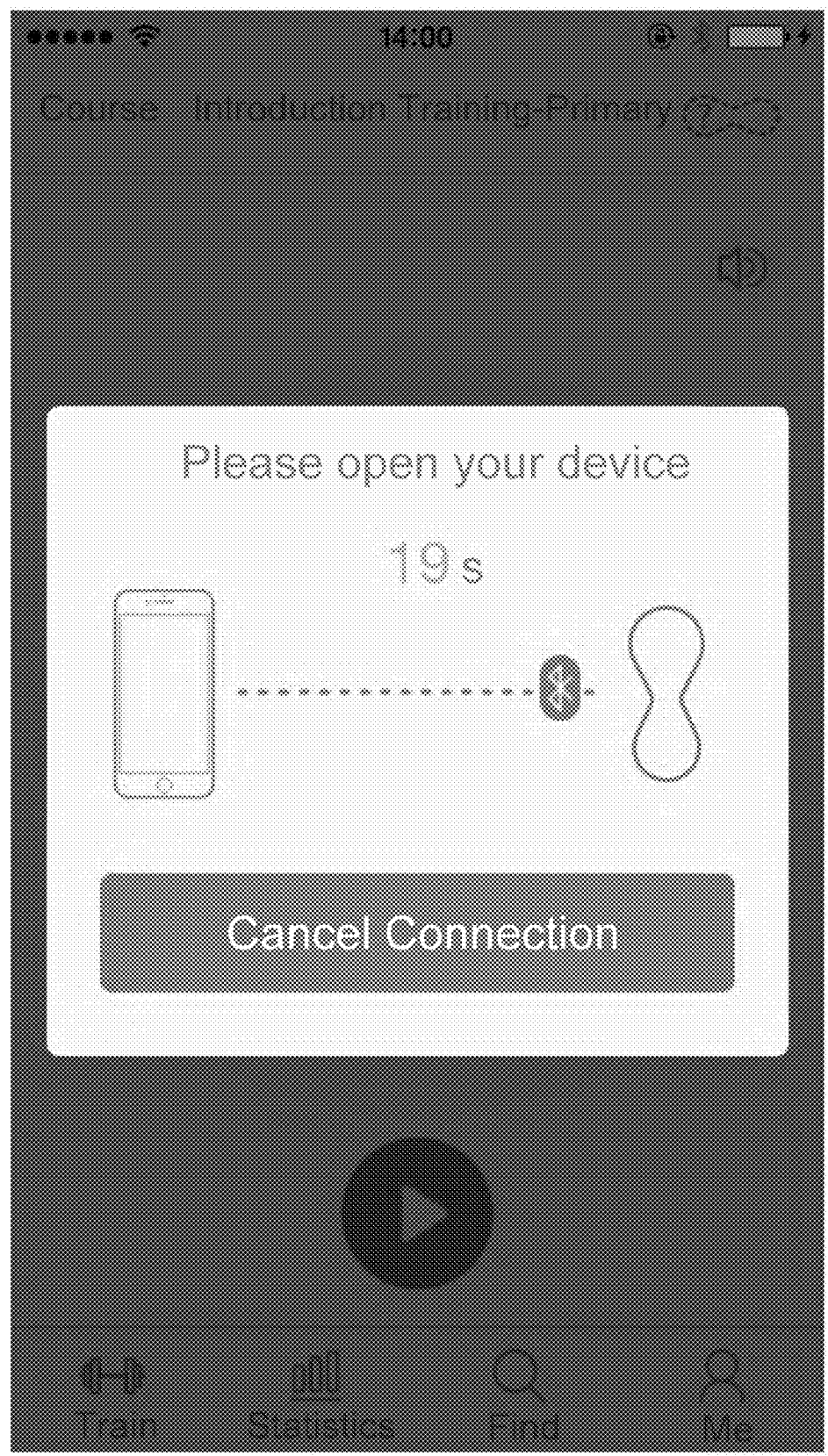
FIG. 25 is an interface when the user starts to establish the connection between the processor and the detector of the physical training system for pelvic floor muscle after the physical training system for pelvic floor muscle is started according to the above preferred embodiment of the present invention.
Figure 26:
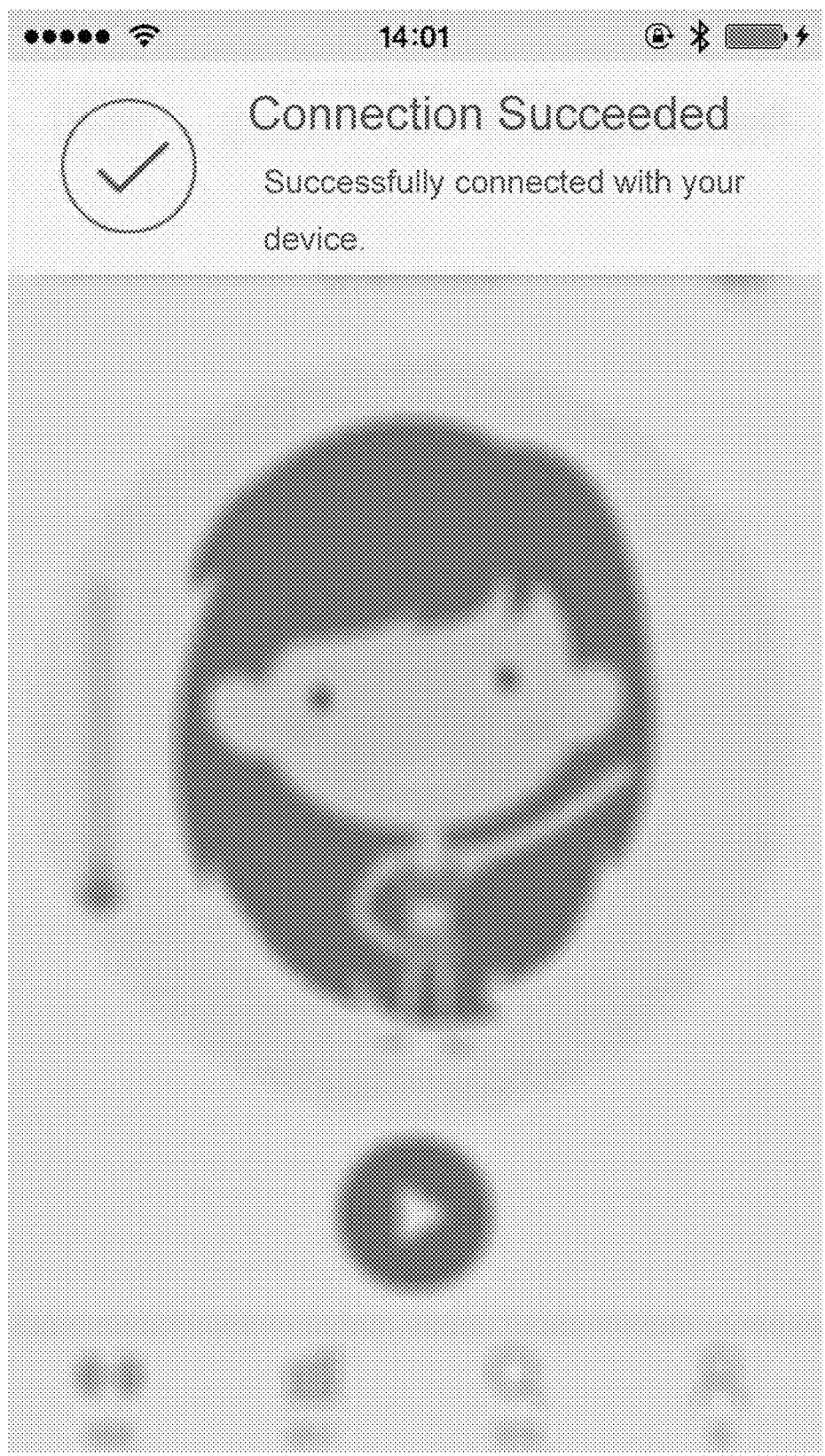
FIG. 26 is a schematic diagram of the successful connection between the processor and the detector of the physical training system for pelvic floor muscle after the physical training system for pelvic floor muscle is started according to the above preferred embodiment of the present invention.
Figure 27:
FIG. 27 is an optional interface of the training courses which is showed on the display screen of the Client of the physical training system for pelvic floor muscle after the physical training system for pelvic floor muscle is started according to the above preferred embodiment of the present invention.
Figure 28:
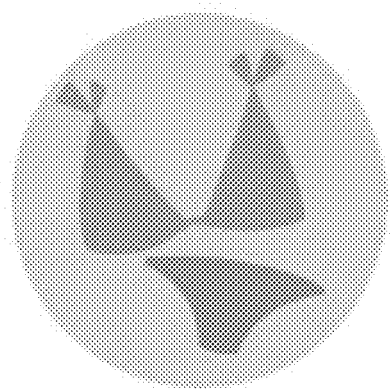
FIG. 28 is an optional interface which is come into the sexy superman training course of the training courses which is showed on the display screen of the Client of the physical training system for pelvic floor muscle after the physical training system for pelvic floor muscle is started according to the above preferred embodiment of the present invention.
Figure 29:
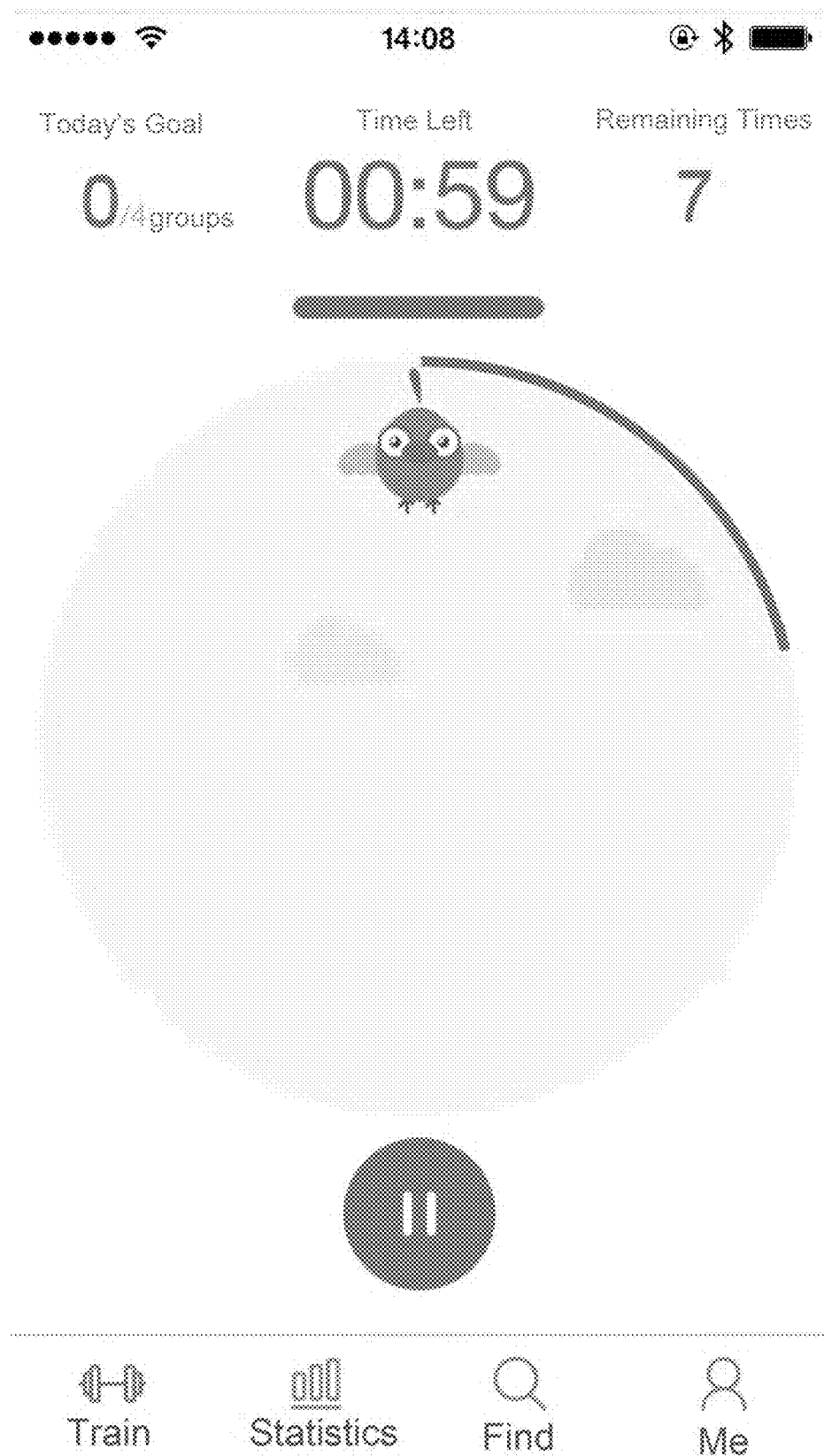
FIG. 29 is a training guiding interface which is showed on the display screen of the Client of the physical training system for pelvic floor muscle after the physical training system for pelvic floor muscle is started and the user chose entering into a training course according to the above preferred embodiment of the present invention.

As shown in FIG. 23 and FIG. 24 of the drawings, the display screen 31 is a touching screen, so the user can select the exercising courses provided by the physical training system pelvic floor muscle through the display screen 31 and accomplish at least one exercising movement according to the guidance of the course content. As shown in FIG. 25 and FIG. 26 of the drawings, when the exercising courses provided by the physical training system for pelvic floor muscle are selected by the user, the display screen of the Client 30 of the physical training system for pelvic floor muscle provides a device for searching and connecting the interface, the user can establish the wireless (or wire) connection between the processor 20 and the detector 10 and the stimulator 40 of the physical training system for pelvic floor muscle through the interface for realizing the communication between the processor 20 and the detector 10. As shown in FIG. 27 and FIG. 28 of the drawings, the user can optionally select and set the exercising settings in the course selecting interface according to his/her hobby.

As shown in FIG. 19 to FIG. 28 of the drawings, the physical training system for pelvic floor muscle can provide different exercising courses to the user, every exercising course has a plurality of grades, the grade is respectively corresponded to exercising setting, as shown in table 1 to table 6:

TABLE 1 the exercising setting which is corresponding to each grade of the introductory training course

| | Exercising movement | Exercising guidance | Exercising auxiliary | Exercising feedback |
| --- | --- | --- | --- | --- |
| Primary grade | Contraction-relaxation | Voice guidance | Vibrator | Comprehensive score |
| Middle grade | Contraction-relaxation | Voice guidance | Vibrator | Comprehensive score |
| High grade | Contraction-relaxation | Voice guidance | Vibrator | Comprehensive score |
| Master grade | Contraction-relaxation | Voice guidance | Vibrator | Comprehensive score |

TABLE 2 the exercising setting which is corresponding to each grade of the sexy superman training course

| | Exercising movement | Exercising guidance | Exercising auxiliary | Exercising feedback |
| --- | --- | --- | --- | --- |
| Primary grade | Contraction-relaxation | Voice guidance | Vibrator | Comprehensive score |
| Middle grade | Contraction-relaxation | Voice guidance | Vibrator | Comprehensive score |
| High grade | Contraction-relaxation | Voice guidance | Vibrator | Comprehensive score |
| Master grade | Contraction-relaxation | Voice guidance | Vibrator | Comprehensive score |

TABLE 3 the exercising setting which is corresponding to each grade of the baby plan training course

| | Exercising movement | Exercising guidance | Exercising auxiliary | Exercising feedback |
| --- | --- | --- | --- | --- |
| Primary grade | Contraction-relaxation | Voice guidance | Vibrator | Comprehensive score |
| Middle grade | Contraction-relaxation | Voice guidance | Vibrator | Comprehensive score |
| High grade | Contraction-relaxation | Voice guidance | Vibrator | Comprehensive score |
| Master grade | Contraction-relaxation | Voice guidance | Vibrator | Comprehensive score |

TABLE 4 the exercising setting which is corresponding to each grade of the fresh hot mama training course

| | Exercising movement | Exercising guidance | Exercising auxiliary | Exercising feedback |
| --- | --- | --- | --- | --- |
| Primary grade | Contraction-relaxation | Voice guidance | Vibrator | Comprehensive score |
| Middle grade | Contraction-relaxation | Voice guidance | Vibrator | Comprehensive score |
| High grade | Contraction-relaxation | Voice guidance | Vibrator | Comprehensive score |
| Master grade | Contraction-relaxation | Voice guidance | Vibrator | Comprehensive score |

TABLE 5 the exercising setting which is corresponding to each grade of the postpartum rehabilitation training course

| | Exercising movement | Exercising guidance | Exercising auxiliary | Exercising feedback |
| --- | --- | --- | --- | --- |
| Primary grade | Contraction-relaxation | Voice guidance | Vibrator | Comprehensive score |
| Middle grade | Contraction-relaxation | Voice guidance | Vibrator | Comprehensive score |
| High grade | Contraction-relaxation | Voice guidance | Vibrator | Comprehensive score |
| Master grade | Contraction-relaxation | Voice guidance | Vibrator | Comprehensive score |

TABLE 6 the exercising setting which is corresponding to each grade of the power of love training course

| | Exercising movement | Exercising guidance | Exercising auxiliary | Exercising feedback |
| --- | --- | --- | --- | --- |
| Primary grade | Contraction-relaxation | Voice guidance | Vibrator | Comprehensive score |
| Middle grade | Contraction-relaxation | Voice guidance | Vibrator | Comprehensive score |
| High grade | Contraction-relaxation | Voice guidance | Vibrator | Comprehensive score |
| Master grade | Contraction-relaxation | Voice guidance | Vibrator | Comprehensive score |

As shown the above table 1 to table 3, the physical training system for pelvic floor muscle can provide at least six different exercising courses, every exercising course has at least four grades, wherein each grade of the every exercising course is respectively correspond to the optional exercising setting (combination) 101, such as the exercising movement setting 1011, the exercising guidance setting 1015, the exercising auxiliary setting 1016 and the exercising feedback setting 1017 an so on, in order to make the user can select a exercising setting (combination) 101 provided on advance when the user selects one grade of one exercising course of the physical training system for pelvic floor muscle to do exercising, in order to make the user do exercising under the guidance of the physical training system for pelvic floor muscle. Preferably, the exercising setting (combination) 101 further comprises the exercising time setting 1012, the exercising intensity setting 1013 and the exercising frequency setting 1014. For example, the exercising time setting 1012 and the exercising frequency setting 1014 of the primary training of the introductory training course can be set to contract 2 s and relax 4 s, the exercising frequency setting 1014 is provided to repeat four circulations of the movement of the contraction-relaxation in every minute. Understandably, the users can also set the specific parameters of the exercising setting (combination) 101 of the physical training system for pelvic floor muscle by themselves.

Fourth Segment: Exercising Guidance

As shown in FIG. 25 to FIG. 29 of the drawings, the display screen 31 of the Client 30 of the physical training system for pelvic floor muscle displays an exercising waiting interface after the user selects or sets the exercising courses, and after the user selects (or clicks) the button of the exercising waiting interface, the physical training system for pelvic floor muscle enters into the procedure of the exercising guidance and guides the user to exercise his/her pelvic floor muscle.

The physical training system for pelvic floor muscle preferably guides the user to exercise his/her pelvic floor muscle through the voice guidance.

Fifth Segment: Feedback Mode

Figure 30:
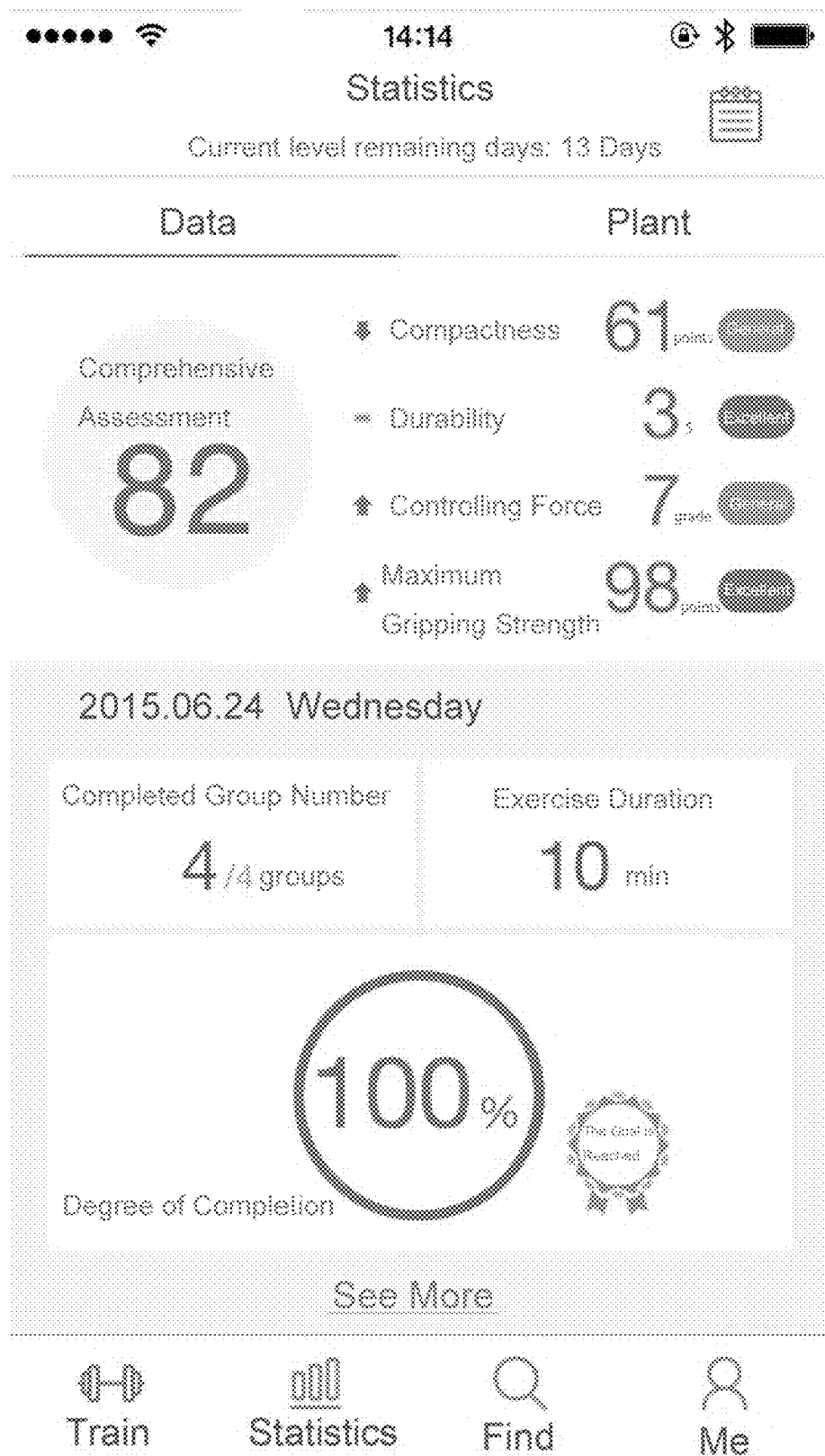
FIG. 30 is a feedback interface of the training result which is showed on the display screen of the Client of the physical training system for pelvic floor muscle after the user complete a training movement or a plurality of training movements according to the above preferred embodiment of the present invention.
Figure 31:
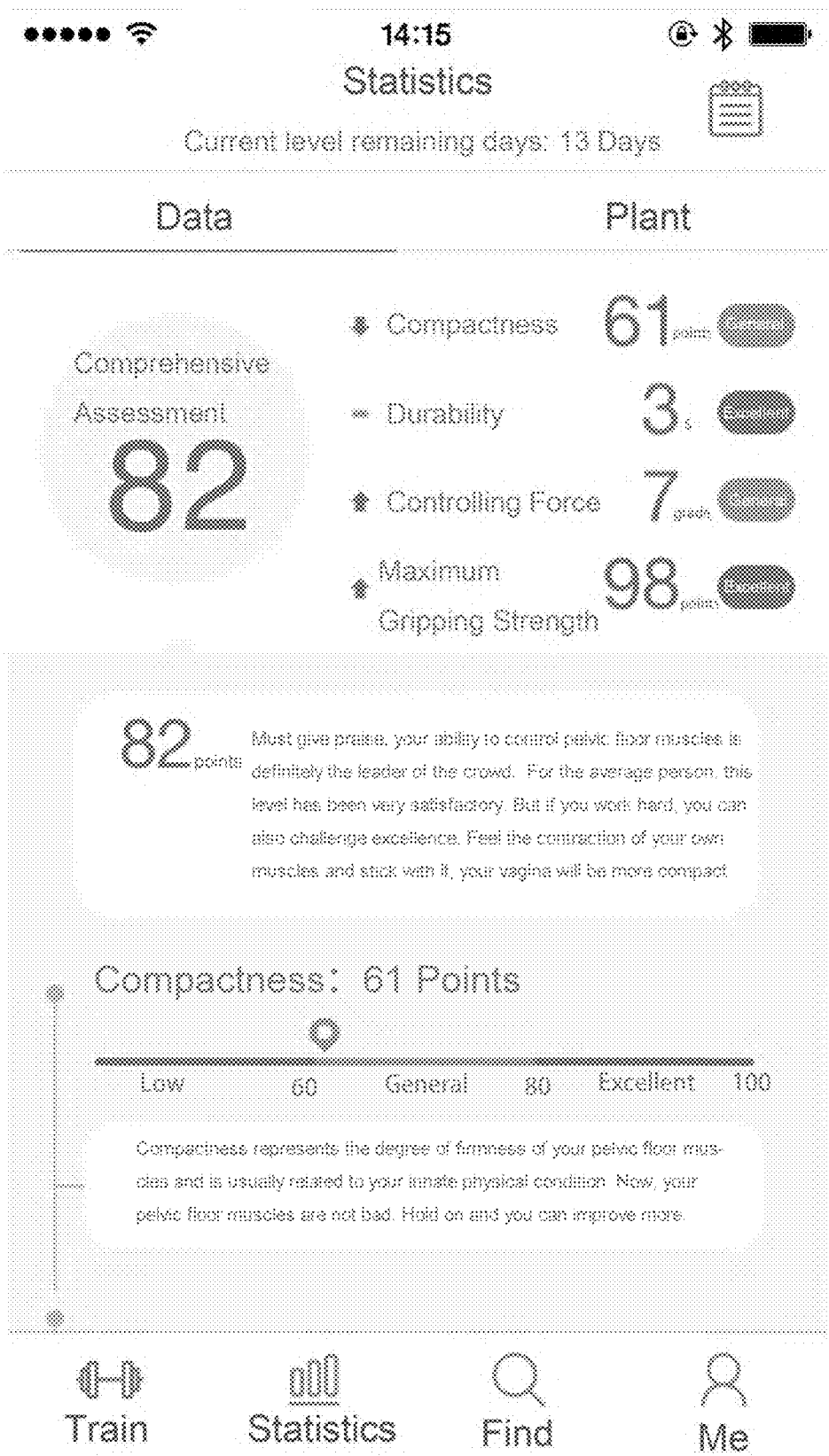
FIG. 31 is a feedback interface of the training result which is showed on the display screen of the Client of the physical training system for pelvic floor muscle after the user complete a training movement or a plurality of training movements according to the above preferred embodiment of the present invention.

As shown in FIG. 30 and FIG. 31 of the drawings, when the user accomplishes one exercising movement or a plurality of exercising movements, the physical training system for pelvic floor muscle will feedback to the user the completing situation of the current exercising, which will be displayed on the display screen 31 of the Client 30, so that the user can evaluate his/her own exercising according to the completing situation of the current exercising, and guide and/or stimulate the user to do exercising continually. As shown in FIG. 30 and FIG. 31 of the drawings, the situation of the current exercising comprises but not limit to the completing evaluation (or score) of the current exercising, planned exercising time (day), accumulated exercising time (day), today's completion of the exercising movement (combination), total exercising time (minute) and average exercising time (minute). In other words, the feedback of the exercising result is displayed on the display screen 31 of the Client 30 of the physical training system for pelvic floor muscle for making the feedback of the exercising result can be sensed by the user, so that the user can evaluate his/her own exercising this time according to the feedback of the current exercising result. The completing evaluation (or score) of the current exercising comprises but not limit to the compactness inside of the user's vagina, the durability of the movement, the controlling force and the detecting result of the maximum gripping strength (or evaluation or score).

Sixth Segment: Initialization

The detector 10 of the physical training system for pelvic floor muscle may be firstly initialize processed when the physical training system for pelvic floor muscle is started to be used in order to the pressure Fc which is applied on the thin film pressure sensor 121 of the detector 10 by the detector.

Seventh Segment: Cloud

As shown in FIG. 1 of the drawings, the physical training system for pelvic floor muscle further comprises a Cloud 50 which is adopted store data. The Cloud 50 is capable of collecting and storing the exercising messages sent by the physical training system for pelvic floor muscle through the electronic communication network, wherein the exercising message comprises the message of the user's personal situation, the message of the exercising setting and/or exercising result of the user's exercising for pelvic floor muscle. Optionally, the Cloud 50 is capable of collecting or storing the exercising messages sent by the physical training system for pelvic floor muscle through the data line. There is a mass of data messages produced in the process of the user's training. For the data, the user can store selectively the data in the processor 20 of the physical training system for pelvic floor muscle, the portable device and/or the Cloud according to the category of the data. After the user's data message is collected to the Cloud 50, the data message can be screened and analyzed for obtaining the data messages aimed at different persons, such as the age, the race, the exercising grade and so on. It will obtain the analyzing results which have a value of application through the further analyzing of the data messages, for example, the analyzing result applied to the clinic and so on.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A physical training system for pelvic floor muscle, comprising:

a detector which comprises a receiving body, a pressure detector which comprises a plurality of thin film sensors provided at said receiving body, a data processing unit, a plurality of force transmitting elements respectively provided on said thin film sensors, and a coat having an inner wall, wherein said receiving body is provided within said coat, wherein each of said plurality of thin film sensors is electrically connected to said data processing unit and has an inductive side, wherein each of said force transmitting elements is provided between said thin film sensors and said inner wall of said coat, wherein each of said force transmitting elements has an operating side being pressed against one of said thin film sensors and an outer side shaped to match with said receiving body, wherein said operating side of each of said force transmitting elements is shaped to match with said inductive side of said thin film sensor, wherein said force transmitting elements are protruded to said inner wall of said coat;

a processor communicated with said detector; and a Client, wherein said physical training system for pelvic floor muscle is capable of providing at least one optional exercising setting to a user for enabling said physical training system for pelvic floor muscle to guide the user to accomplish at least one exercising movement, wherein said exercising setting is selected from a group of exercising settings, wherein said group of exercising settings comprises an exercising movement setting, an exercising time setting, an exercising intensity setting, an exercising frequency setting, an exercising guidance setting, an exercising auxiliary setting and an exercising feedback setting, wherein said exercising settings is capable of being displayed on said Client.

2. The physical training system, as recited in claim 1, wherein said physical training system for pelvic floor muscle is further capable of providing said exercising settings according to the user's personal situation, wherein said personal situation is selected from a combination of personal situations, wherein said combination of personal situations comprises an age status, a historical data status, a current detecting data status and an exercising purpose status.

3. The physical training system, as recited in claim 2, wherein said detector is provided to detect contractility of vaginal inner wall of the user and generate a real-time detecting data, and send said real-time detecting data to said processor, said processor is capable of receiving and processing said real-time detecting data and obtain a current detecting data status, and provide said exercising settings according to said current detecting data status.

4. The physical training system, as recited in claim 3, wherein said receiving body defines a receiving chamber, said pressure detector is provided within said receiving body, said data processing unit is provided within said receiving chamber, wherein said pressure detector is provided to detect pressure which is applied on said pressure detector by vaginal inner wall and generate a real-time detecting signal, said data processing unit is capable of receiving said real-time detecting signal from said pressure detector and transmit said real-time detecting signal to said processor.

5. The physical training system, as recited in claim 4, wherein said data processing unit comprises a first communicating module, wherein said first communicating module of said data processing unit is capable of receiving said realtime detecting signal from said pressure detector and transmit said real-time detecting signal to said processor, wherein said thin film sensors are electrically connected in parallel and are electrically connected to said first communicating module.

6. The physical training system, as recited in claim 5, wherein every said thin film pressure sensor is provided to detect pressure which is applied on said pressure detector by vaginal inner wall and generate said real-time detecting signal.

7. The physical training system, as recited in claim 5, wherein said receiving body has an outer wall and comprises a plurality of installing positions provided on said outer wall of said receiving body, wherein every said outer wall has an installing surface, wherein every said thin film pressure sensor of said pressure detector is respectively provided on said installing surface.

8. The physical training system, as recited in claim 7, wherein every said thin film pressure sensor has an installing side, wherein said installing side is provided on said installing position of said receiving body.

9. The physical training system, as recited in claim 2, wherein said coat has an operating room, wherein said receiving body is provided within said operating room.

10. The physical training system, as recited in claim 8, wherein said coat has an operating room, wherein said receiving body is provided within said operating room.

11. The physical training system, as recited in claim 10, wherein every said force transmitting element is provided on said inner wall of said coat in the form of integral.

12. The physical training system, as recited in claim 5, wherein said data processing unit of said detector further comprises a signal transforming module, wherein said signal transforming module is connected electrically with said pressure detector and said first communicating module respectively, wherein said signal transforming module is capable of receiving said real-time detecting signal from said pressure detector and make said real-time detecting signal to be transmitted from analog electronic signal into figure signal, wherein said first communicating module is capable of receiving said real-time detecting signal from said signal transforming module.

13. The physical training system, as recited in claim 12, wherein said data processing unit further comprises a signal amplifying module, wherein said signal amplifying module is connected electrically with said signal transforming module and said pressure detector respectively, wherein said signal amplifying module is provided to amplify detecting signal from said thin film pressure sensors of said pressure detector.

14. The physical training system, as recited in claim 5, wherein said processor comprises a data processing module and a second communicating module connected electrically to said data processing module, wherein said second communicating module is communicated with said first communicating module of said data processing unit, so that said second communicating module is capable of receiving said real-time detecting data from said first communicating module of said data processing unit and sending said real-time detecting data to said data processing module of said processor.

15. The physical training system, as recited in claim 13, wherein said processor is capable of calculating pressure F which is applied on every said thin film pressure sensor by the user's vagina through following formula:

$$Fs-b=-(VT*RF)/(a*Vout);$$

F=Fs−Fc; wherein said Vout is measuring voltage, said VT is voltage loaded into said thin film pressure sensors, said RF is resistance of said signal amplifying module, said a and b are characteristic constants of said thin film pressure sensors, said Fc is pressure detected by said thin film pressure sensors of said detector in the case of said coat of said detector is not imposed pressure, wherein said real-time detecting data at least comprises said voltage VT which is loaded into said thin film pressure sensors of said pressure detector.

16. The physical training system, as recited in claim 9, wherein said physical training system for pelvic floor muscle further comprises a stimulator, and said coat further forms a vibrating room, wherein said stimulator is provided within said vibrating room.

17. A method of guiding exerciser to exercise pelvic floor muscle, comprising the following steps:

(a1) detecting contractility of vaginal inner wall and generating a real-time detecting data by using a detector of a physical training system for pelvic floor muscle, and sending said real-time detecting data to a processor of said physical training system for pelvic floor muscle, wherein said processor is capable of processing said real-time detecting data and generate a current detecting data status, wherein said detector comprises a receiving body, a pressure detector which comprises a plurality of thin film sensors provided at said receiving body, a data processing unit, a plurality of force transmitting elements respectively provided on said thin film sensors, and a coat having an inner wall, wherein said receiving body is provided within said coat, wherein each of said plurality of thin film sensors is electrically connected to said data processing unit and has an inductive side, wherein each of said force transmitting elements is provided between said thin film sensors and said inner wall of said coat, wherein each of said force transmitting elements has an operating side being pressed against one of said thin film sensors and an outer side shaped to match with said receiving body, wherein said operating side of each of said force transmitting elements is shaped to match with said inductive side of said thin film sensor, wherein said force transmitting elements are protruded to said inner wall of said coat, wherein said data processing unit comprises a first communicating module, wherein said first communicating module of said data processing unit is capable of receiving said real-time detecting signal from said pressure detector and transmit said real-time detecting signal to said processor, wherein said thin film sensors are electrically connected in parallel and are electrically connected to said first communicating module;

(a) providing at least one optional exercising setting according to an exerciser's personal situation; and (b) providing a guidance of exercising movement to exerciser for guiding a user accomplishing at least one exercising movement after said exerciser chooses an exercising setting.

18. The method of guiding exerciser to exercise pelvic floor muscle, as recited in claim 17, further comprising following step:

(c) providing an exercising result feedback displayed on a display screen of a Client according to completing situation of the user's exercising, wherein said step (c) is located after said step (b).

* * * * *